United States Patent [19]
Sikorski et al.

[11] Patent Number: 6,038,475
[45] Date of Patent: Mar. 14, 2000

[54] HIGH OUTPUT SENSOR AND ACCELEROMETER FOR IMPLANTABLE MEDICAL DEVICE

[75] Inventors: James M. Sikorski, Mounds View, Minn.; David A. Ruben, Mesa, Ariz.

[73] Assignee: Medtronic, Inc., Minneapolis, Minn.

[21] Appl. No.: 09/197,721

[22] Filed: Nov. 23, 1998

Related U.S. Application Data

[63] Continuation of application No. 08/950,517, Oct. 14, 1997, Pat. No. 5,911,738, which is a continuation-in-part of application No. 08/904,142, Jul. 31, 1997, Pat. No. 5,885,471, which is a continuation-in-part of application No. 08/399,072, Mar. 8, 1995, Pat. No. 5,674,258.

[51] Int. Cl.$^7$ ..................................... A61N 1/375
[52] U.S. Cl. .................... 607/19; 607/20; 216/2
[58] Field of Search .................... 607/19, 20, 36; 216/2

[56] References Cited

U.S. PATENT DOCUMENTS

| | | |
|---|---|---|
| 4,140,132 | 2/1979 | Dahl . |
| 4,379,459 | 4/1983 | Stein . |
| 4,476,868 | 10/1984 | Thompson . |
| 4,485,813 | 12/1984 | Anderson et al. . |
| 4,556,063 | 12/1985 | Thompson et al. . |
| 4,653,326 | 3/1987 | Danel et al. . |
| 4,679,434 | 7/1987 | Stewart . |
| 4,742,182 | 5/1988 | Fuchs . |
| 4,891,985 | 1/1990 | Glenn . |
| 4,987,781 | 1/1991 | Reimann . |
| 5,014,702 | 5/1991 | Alt . |
| 5,031,615 | 7/1991 | Alt . |
| 5,044,366 | 9/1991 | Alt . |
| 5,052,388 | 10/1991 | Sivula et al. . |
| 5,215,084 | 6/1993 | Schaldach . |
| 5,235,237 | 8/1993 | Leonhardt . |
| 5,309,014 | 5/1994 | Wilson . |
| 5,312,453 | 5/1994 | Shelton et al. . |
| 5,315,204 | 5/1994 | Park . |
| 5,315,205 | 5/1994 | Ohno et al. . |
| 5,318,596 | 6/1994 | Barreras et al. . |
| 5,373,267 | 12/1994 | Kaida et al. . |
| 5,425,750 | 6/1995 | Moberg . |
| 5,595,172 | 1/1997 | Shinohara . |
| 5,674,258 | 10/1997 | Henschel et al. . |
| 5,676,851 | 10/1997 | Suzuki et al. . |
| 5,725,785 | 3/1998 | Ishida et al. . |
| 5,885,471 | 3/1999 | Ruben et al. . |
| 5,896,068 | 4/1999 | Nilsson . |

FOREIGN PATENT DOCUMENTS

| | | |
|---|---|---|
| 0 434 878 A1 | 7/1991 | European Pat. Off. . |
| 0 529 122 A1 | 3/1993 | European Pat. Off. . |
| 86 26 133.9 | 6/1988 | Germany . |
| WO 91/13364 | 9/1991 | WIPO . |
| WO 95/02431 | 1/1995 | WIPO . |
| WO 95/03086 | 2/1995 | WIPO . |

OTHER PUBLICATIONS

Section 5.2: Acceleration Sensors—A Bathch Fabricated Silicon Accelerometer, reprinted from IEEE Trans. Electron Devices, vol. ED–26, No. 12, pp. 1911–1917, Dec. 1979.
*Guide to Modern Piezoelectric Ceramics,* Morgan Matroc, Inc. Electro Ceramics Division, pp 1–27: Rev. 3–93.

*Primary Examiner*—William E. Kamm
*Assistant Examiner*—Carl H. Layno
*Attorney, Agent, or Firm*—Thomas F. Woods; Girma Wolde-Michael; Haold R. Patton

[57] ABSTRACT

An accelerometer and sensor assemblies for medical implantable devices such as pacemakers, cardioverters, IPGs, PCDs, defibrillators, ICDs, and the like, includes at least one intermediate metallization layer sandwiched between a first lower surface of at least one upper sheet formed from a piezoelectric material surface, and a second upper surface of at least one lower sheet formed from a piezoelectric material. The at least one upper sheet has a first outer edge disposed between its first upper and first lower surfaces. The at least one lower sheet has a second outer edge disposed between its second upper and second lower surfaces. The at least one intermediate metallization layer is not disposed at all locations between the first lower surface and the second upper surface, but extends to an external region disposed between the first outer edge and the second outer edge, and is electrically connected to the external region. Various embodiments of the sensor or accelerometer are capable of providing high amplitude output signals and reducing parts and manufacturing costs.

22 Claims, 17 Drawing Sheets

Uncut, unplated, bulk wafer

Before wafer assembly

After wafer assembly (unplated)

Polarization of unplated, uncut assembled bulk wafer

Plating of external surfaces of uncut, assembled bulk wafer

Cut and plated assembled bulk wafer

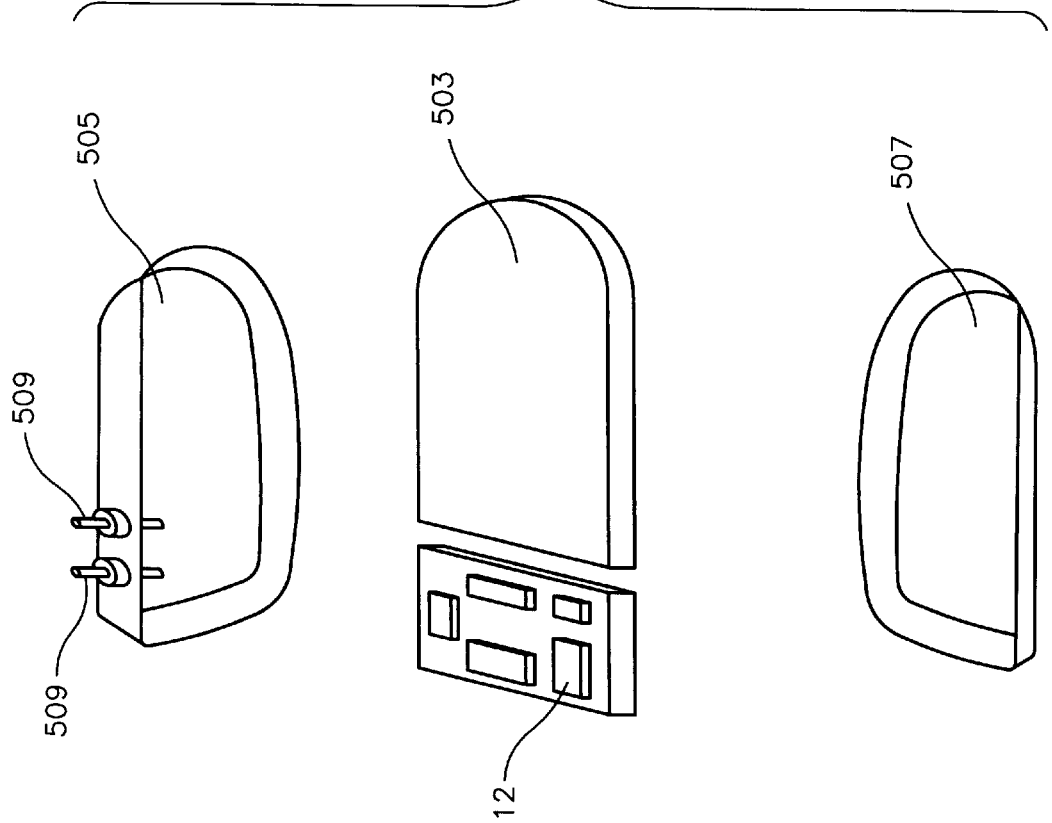

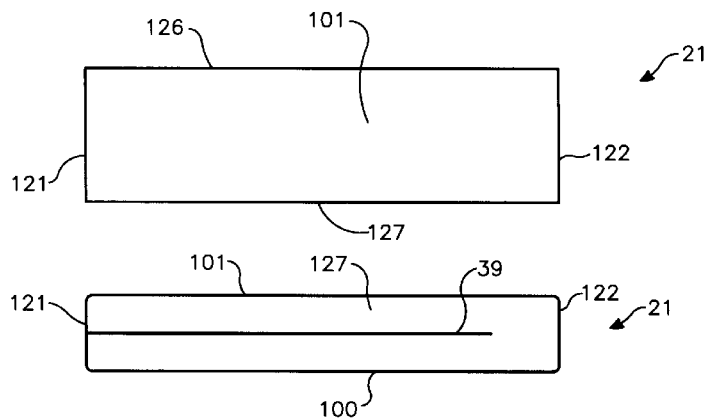
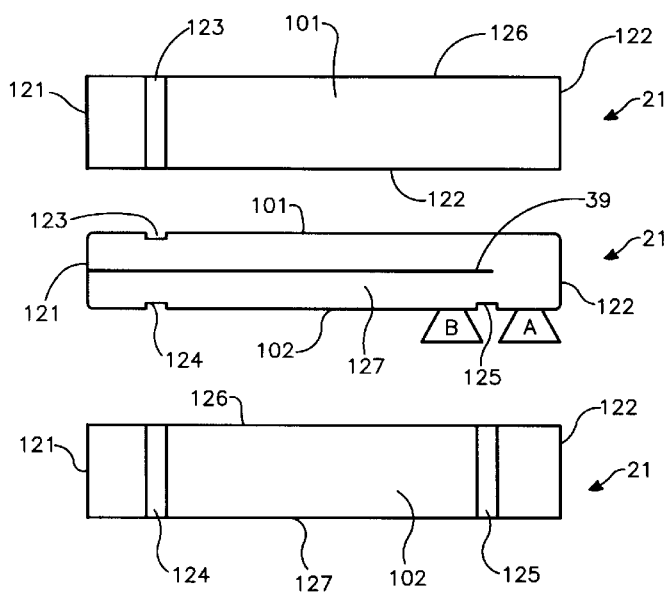
FIG. 6(a)
FIG. 6(b)
FIG. 7(a)
FIG. 7(b)
FIG. 7(c)
FIG. 7(d)

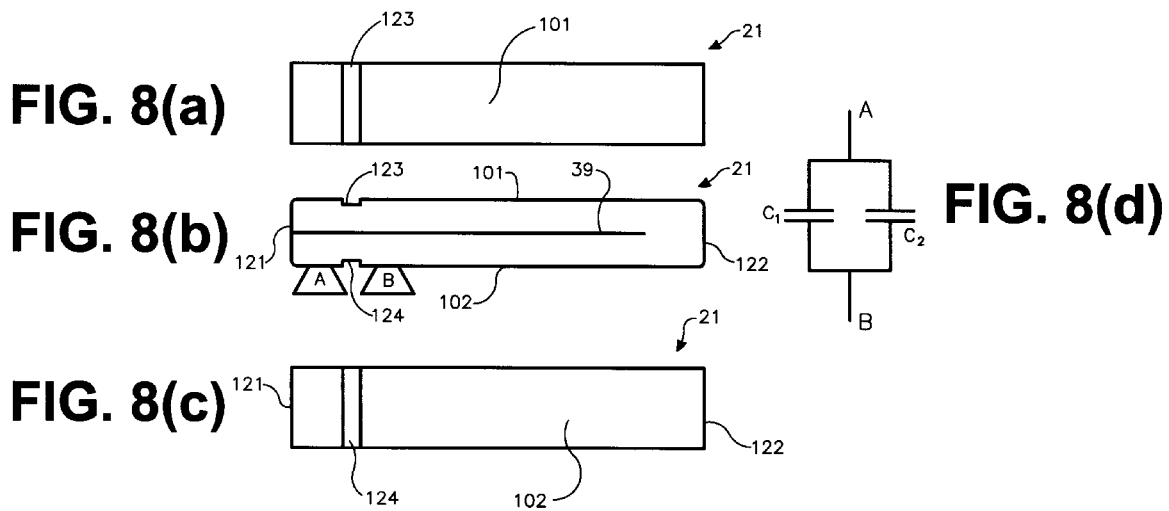

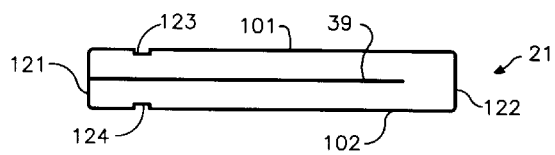
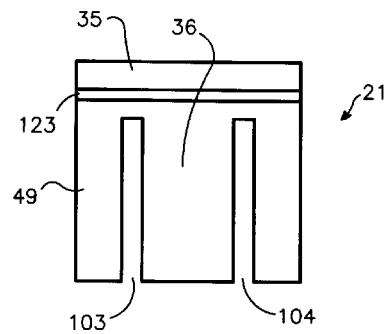
FIG. 9(a)
FIG. 9(b)
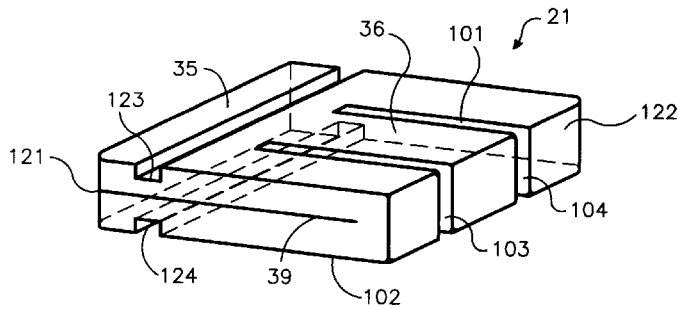
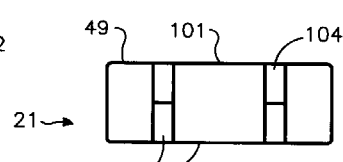
FIG. 9(d)
FIG. 9(c)
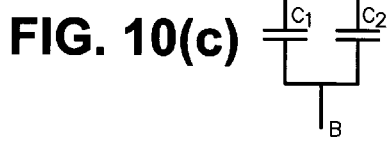
FIG. 10(c)
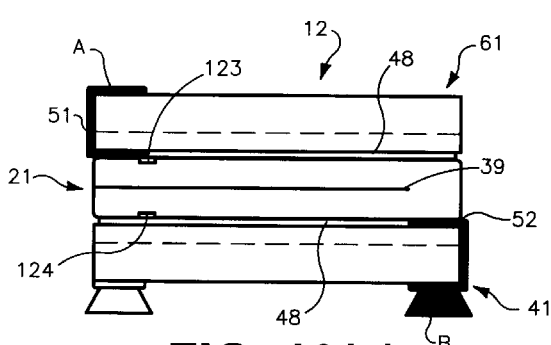
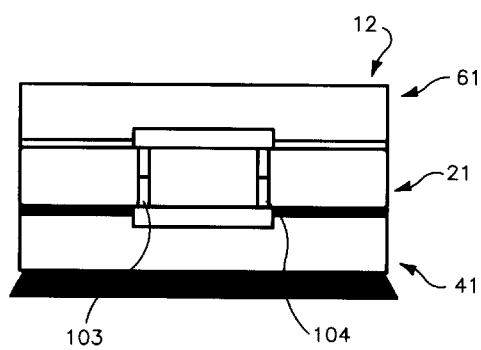
FIG. 10(a)
FIG. 10(b)

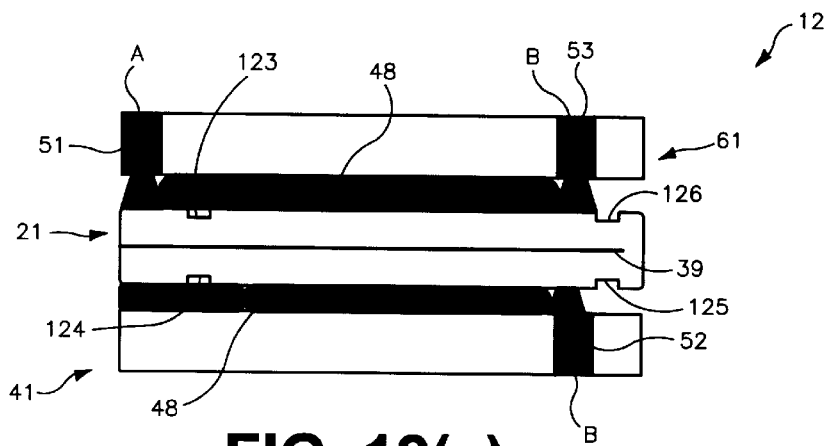
FIG. 12(a)
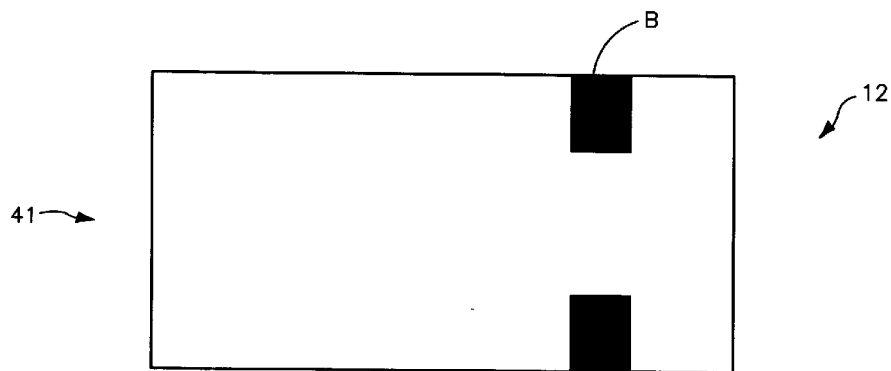
FIG. 12(b)
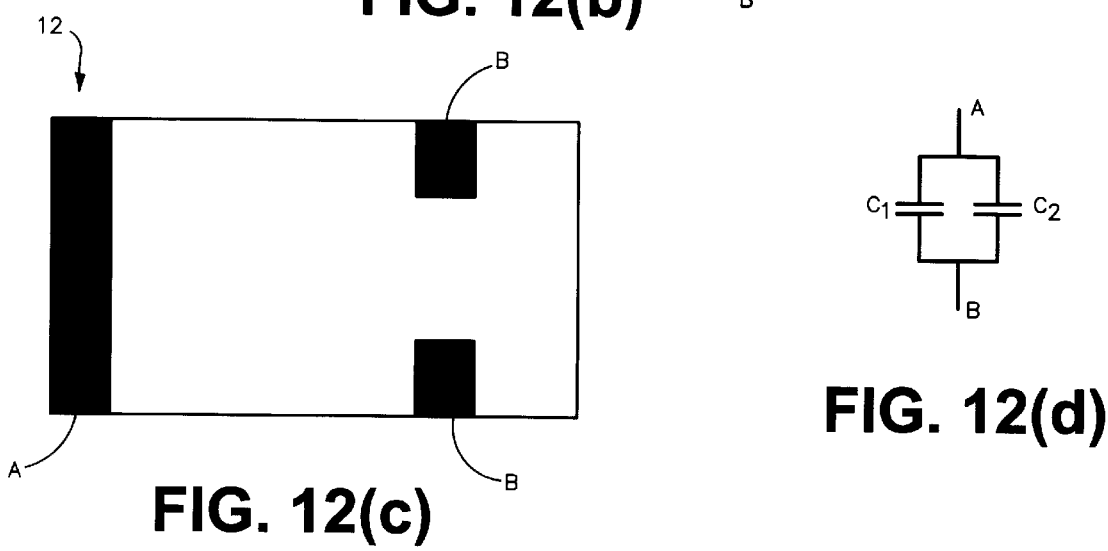
FIG. 12(c)
FIG. 12(d)

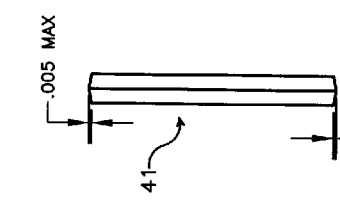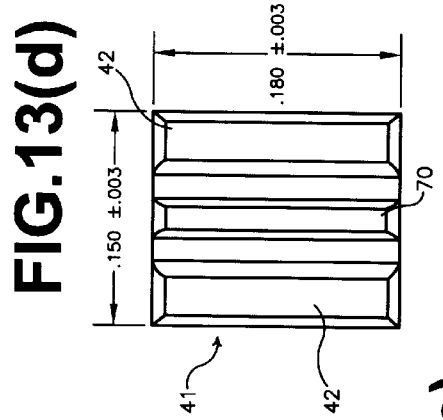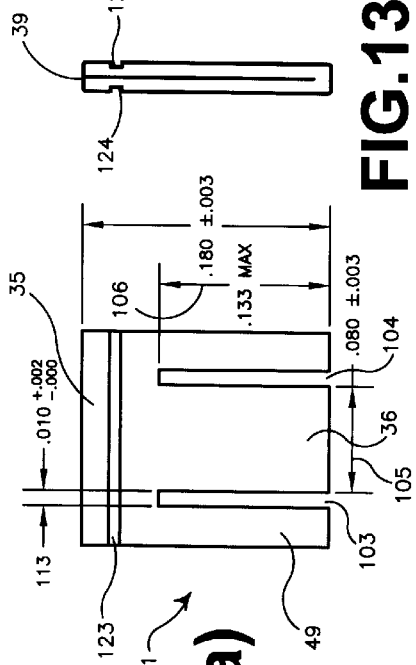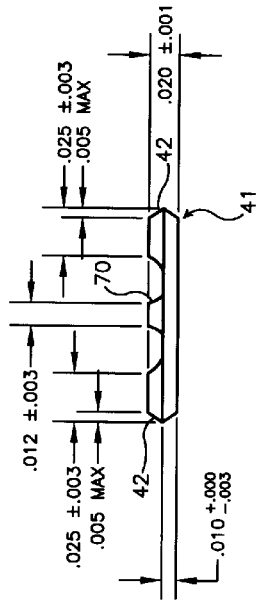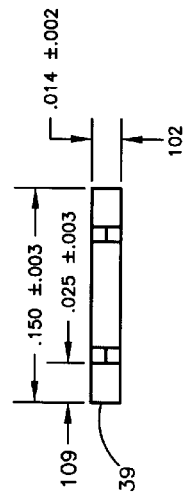

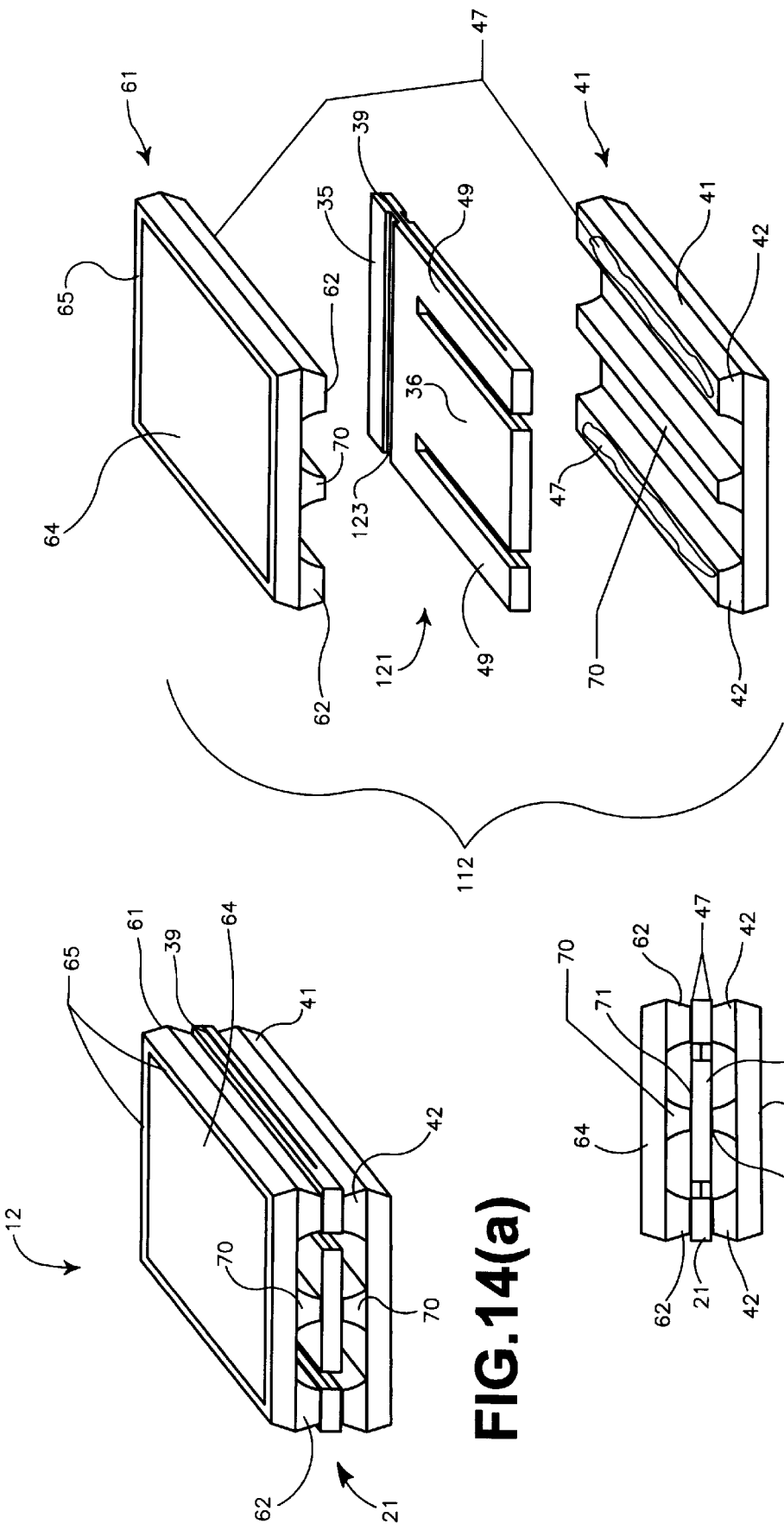

HIGH OUTPUT SENSOR AND ACCELEROMETER FOR IMPLANTABLE MEDICAL DEVICE

CROSS-REFERENCE TO RELATED APPLICATION

This patent application is a continuation of U.S. patent application Ser. No. 08/950,517, now U.S. Pat. No. 5,911,738, to Sikorski et al. filed Oct. 14, 1997 entitled "High Output Sensor and Accelerometer for Implantable Medical Device", which is a continuation-in-part of U.S. patent application Ser. No. 08/904,142, now U.S. Pat. No. 5,885,471, to Reuben et al. filed Jul. 31, 1997 entitled "Shock Resistant Accelerometer for Implantable Medical Device," which is a continuation-in-part of U.S. patent application Ser. No. 08/399,072, now U.S. Pat. No. 5,674,258, to Henschel et al. filed Mar. 8, 1995 entitled "Packaged Integrated Accelerometer", the disclosure of which is hereby incorporated by reference herein in its entirety.

BACKGROUND OF THE INVENTION

The present invention relates generally to sensors, including accelerometers, and finds particularly efficacious application in implantable cardiac pacemakers as a sensor for generating an electrical output signal indicative of a patient's activity.

The use of piezoceramic cantilevered beams is well known in the art of cardiac pacing, as are the equations which govern their response characteristics. Conventional electrical and mechanical connection of such a beam is typically accomplished by clamping onto the short edge of the beam to produce a cantilever configuration defining an overall beam length.

U.S. Pat. No. 4,140,132 to Dahl describes piezoceramic material in a physical activity sensor or accelerometer An elongated piezoelectric cantilevered element is disclosed as having a weighted mass on one end of the element and being enclosed within an implanted cardiac pacemaker.

U.S. Pat. No. 4,896,096 to Nilsson describes an activity sensor of the flexural type, where a piezoelectric element is composed of two individual piezoceramic parts arranged side-by-side and that are oppositely polarized.

U.S. Pat. No. 5,235,237 to Leonhardt discloses a piezoceramic bending beam accelerometer enclosed within a housing where surface mount technology is employed. One end of the packaged accelerometer is clamped down within an enclosed package.

U.S. Pat. No. 4,653,326 to Danel et al. describes an accelerometer capable of measuring a component of acceleration by means of a variable capacitance capacitor.

U.S. Pat. No. 5,031,615 to Alt discloses a pacemaker employing an accelerometer comprising a miniaturized mechano-electrical converter or transducer formed in a semiconductor device.

U.S. Pat. No. 5,044,366 to Alt discloses a cardiac pacemaker for implantation in a patient that utilizes a pair of sensors.

U.S. Pat. No. 5,425,750 to Moberg discloses a multi-axis physical activity sensor for use with a rate-responsive pacemaker and a method for fabricating same.

The inventions disclosed in preceding references are all incorporated by reference herein in their respective entireties.

At least some of the inventions disclosed in the preceding references possess certain disadvantages. For example, the beam connection to the package or pacemaker shield may become a dominant factor in determining the sensitivity of the accelerometer when employing a bonding medium of either solder or conductive epoxy. When bonding the medium may bleed onto the beam and result in a reduced effective net length of the beam as well as attenuation of piezoceramic sensitivity. Hence, the bonding step can adversely affect the overall beam performance and contribute to manufacturing yield loss. Additionally, many bonding methods require complex and expensive packing techniques to ensure a robust design.

Some prior art pacemaker accelerometers suffer from excessive mechanical fragility to the extent that the center cantilever beams thereof break, fracture or otherwise fail when the pacemakers are dropped onto hard surfaces from heights of only a few feet or inches. Finally, many prior art pacemaker accelerometers provide relatively low voltage output signals, and thus may provide output signals having unacceptably low or marginally acceptable signal-to-noise ratios.

At least some of the above-described devices described in the foregoing references may be modified advantageously by employing the teachings set forth below concerning the present invention.

SUMMARY OF THE INVENTION

The present invention overcomes the disadvantages of the prior art by providing a method of and apparatus for coupling an accelerometer within a cardiac pacemaker, and by providing a structure which improves substantially the shock survivability of same.

The present invention has certain objects. That is, the present invention provides solutions to certain problems existing in the prior art such as implantable medical devices having accelerometers disposed therein that: (a) are excessively fragile or prone to fracturing, breakage or failure; (b) may break off, or have portions thereof that may break off, in response to a high acceleration event, the broken accelerometer or portion thereof potentially shorting out electrical or electronic circuitry disposed within the implantable medical device; (c) are insufficiently reliable; (d) are prone to fracturing, breakage or other failure during manufacturing, final assembly, transportation or shipping, handling, implantation, or during ordinary operation while implanted in a human subject; (e) do not permit or only with difficulty permit electrical or mechanical connection to the center electrode thereof; (f) are expensive to package; (g) have high piece part costs; (h) provide poor or marginal electrical output performance respecting signal-to-noise and other characteristics; (I) may depole or depolarize spontaneously under high temperatures and thereafter remain unrepolable or unrepolarizable; (j) may be insufficiently resistant to shock, and (k) provide output signals having low amplitudes.

The accelerometer assembly of the present invention provides certain advantages, including: (a) decreased susceptibility to fracturing, breakage or other failure during manufacturing, final assembly, transportation or shipping, handling, implantation, or during ordinary operation while implanted in a human subject; (b) a low cost simple solution to the problems existing in the prior art: (c) surface mountability; (d) easy and simple cleaning of the internal cavity thereof, either before or after surface mounting to remove solidified droplets of solder, flux residue and the like; (e) increased reliability of implantable medical devices such as pacemakers, cardioverters, IPGs (implantable pulse generators), PCDs (pacer-cardioverters), defibrillators, ICDs (implantable cardioverter-defibrillator) and the like containing the assembly; (f) the same or substantially the same output voltage as prior art devices, notwithstanding its various other advantages; (g) substantially increased output voltages; (h) output signals having increased signal-to-noise ratios; (I) an ability to repole, repolarize, depole or depolarize the piezoelectric layers of the accelerometer assembly after the assembly has been manufactured and assembled, and in a controlled fashion; (j) a center electrode or internal electrically conductive layer that is accessible for electrical and mechanical connection thereto; (k) an accelerometer assembly that may be connected electrically and mechanically to implantable medical device circuitry by means of electrically conductive epoxy, solder or other suitable material disposed on one side only of the assembly or disposed in one general area only of the assembly; (l) easier and less expensive packaging of the assembly: and (m) reduced risk and increased safety for patients owing to increased reliability and reduced incidence of failure of the accelerometer assembly.

The accelerometer assembly of the present invention has certain features, including: (a) an internal electrically conductive layer disposed between sheets of piezoelectric material; (b) an internal electrically conductive layer that is not present at all locations between sheets of adjoining piezoelectric material: (c) portions of adjoining piezoelectric sheets that directly contact one another; (d) an internal electrically conductive layer that extends between sheets of piezoelectric material to an external region disposed between the outer edges of the sheets; (e) a piezoelectric sub-assembly comprising a first generally planar layer formed from piezoelectric material, a second generally planar layer formed from piezoelectric material, and an internal electrically conductive layer, (f) an external electrically conductive layer that covers at least portions of the piezoelectric sub-assembly; (g) an external electrically conductive layer that covers at least portions of, and that is electrically connected to, the external region of the internal electrically conductive layer, and (h) an external electrically conductive layer that has been cut or laser-scribed in at least two non-contiguous locations to yield at least first and second electrically conductive regions of a piezoelectric sub-assembly that are electrically isolated from one another.

In a preferred embodiment of the present invention, an accelerometer assembly comprises at least three electrodes electrically isolated from one another in a piezoelectric sub-assembly. The sub-assembly is covered at least partially with an external electrically conductive layer that has been laser scribed or cut to provide electrical isolation of each of the electrodes from the other electrodes. At least one of the electrodes is an internal electrode disposed between opposing sheets of piezoelectric material, and forms an internal electrically conductive layer to which electrical connection is possible from the external surface of the sub-assembly. The remaining at least two electrodes are external electrodes. The at least two external electrodes may be connected electrically in parallel across the internal electrode to provide a high output signal.

Other features, advantages and objects of the present invention will become more apparent by referring to the appended drawings, detailed description and claims.

BRIEF DESCRIPTION OF THE DRAWINGS

FIG. 5 shows an exploded perspective view of an implantable medical device of the present invention and its corresponding electronics hermetically sealed therewithin;

FIGS. 6(a) and 6(b) show one embodiment of a piezoelectric subassembly of the present invention, where the piezoelectric sub-assembly has an external electrically conductive layer disposed on at least some of the external surfaces thereof;

FIGS. 7(a) through 7(c) show the piezoelectric sub-assembly of FIGS. 6(a) and 6(b) after it has been subjected to laser scribing or cutting steps and electrically and mechanically connected to electrical connections A and B, where portions of the external electrically conductive layer are electrically isolated from one another to produce one embodiment of an accelerometer of the present invention;

FIG. 7(d) illustrates schematically the electrical configuration of the accelerometer of FIGS. 7(a) through 7(c);

FIGS. 8(a) through 8(c) show the piezoelectric sub-assembly of FIGS. 6(a) and 6(b) after it has been subjected to laser scribing or cutting steps and electrically and mechanically connected to electrical connections A and B, wherein portions of the external electrically conductive layer are electrically isolated from one another to produce another embodiment of an accelerometer of the present invention;

FIG. 8(d) illustrates schematically the electrical configuration of the accelerometer of FIGS. 8(a) through 8(c);

FIGS. 9(a) through 9(d) show selected views of one embodiment of a piezoelectric sub-assembly of the present invention;

FIGS. 10(a) and 10(b) show selected views of an accelerometer assembly incorporating the piezoelectric sub-assembly of FIGS. 9(a) through 9(d) therein;

FIG. 10(c) illustrates schematically the electrical configuration of the accelerometer assembly of FIGS. 10(a) and 10(b);

FIGS. 12(a) through 12(c) show selected views of an accelerometer assembly having the piezoelectric sub-assembly of FIGS. 11(a) through 11(c) disposed therein;

FIG. 12(d) illustrates schematically the electrical configuration of the accelerometer assembly of FIGS. 12(a) through 12(c);

FIGS. 13(a) through 13(f) show selected views and preferred dimensions of one embodiment of an accelerometer assembly of the present invention;

FIGS. 14(a) through 14(c) show selected views of a preferred embodiment of the accelerometer assembly of the present invention;

DESCRIPTION OF THE PREFERRED EMBODIMENTS

Figure 1:
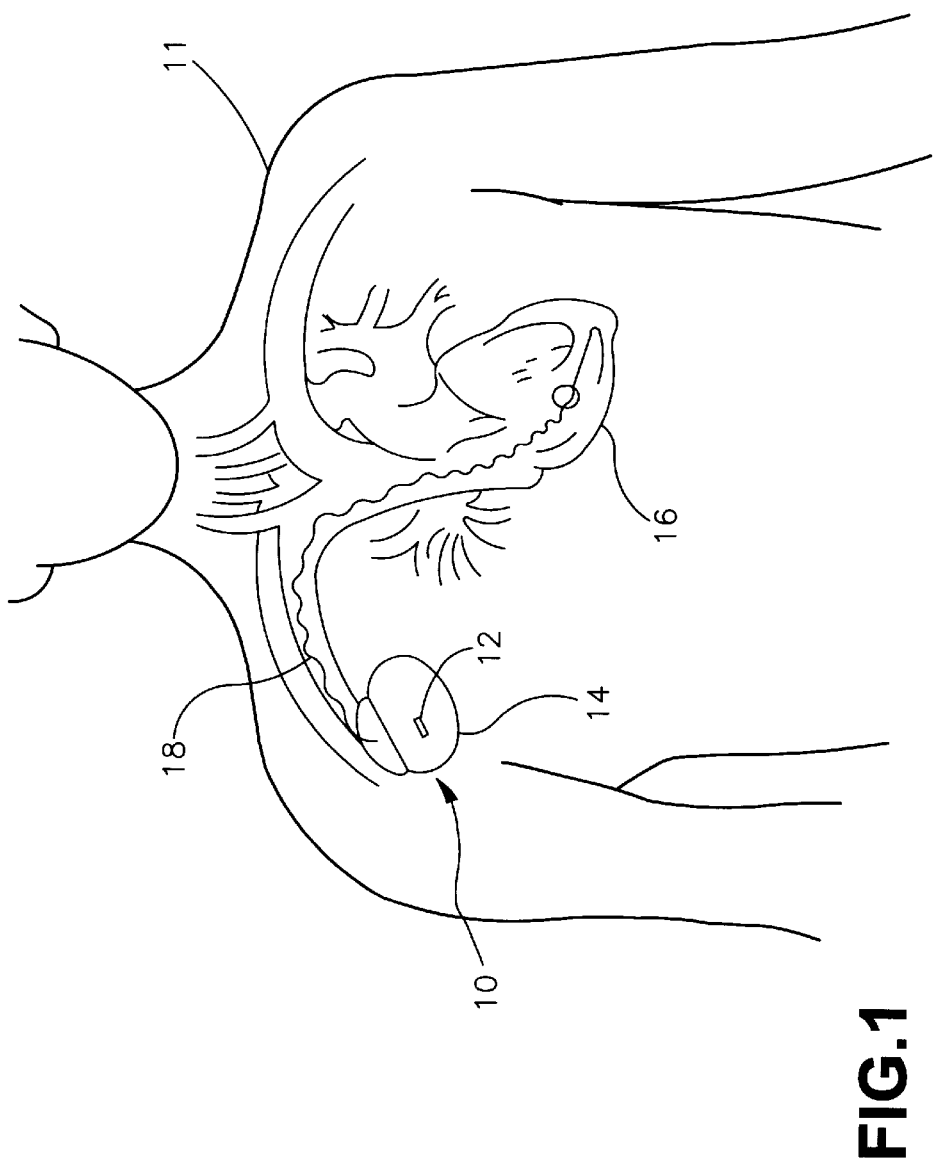
FIG. 1 shows an implantable medical device in accordance with one embodiment of the present invention.

FIG. 1 shows the placement of pacemaker 10 in accordance with one embodiment of the present invention in a human subject. Pacemaker 10 is shown in FIG. 1 as it would be implanted in a patient 11. The preferred embodiment of the invention includes an activity sensor 12, which is a piezoceramic accelerometer disposed on a hybrid circuit and isolated from housing 14 of pacemaker 10. Pacemaker 10 may additionally include other sensors, such as a pressure sensor or the like implanted within heart 16 or disposed on the distal end of pacemaker lead 18.

A pacemaker which measures the physical activity of a patient by means of a piezoelectric transducer disposed on the housing of the pacemaker is disclosed in U.S. Pat. No. 4,485,813 to Anderson et al., hereby incorporated by reference herein in its entirety. U.S. Pat. No. 5,031,615 to Alt discloses another example of an activity-sensing cardiac pacemaker which includes an integrated miniaturized accelerometer.

It is to be understood that the present invention is not limited in scope to either single-sensor or dual-sensor pacemakers, and that other sensors besides activity and pressure sensors could be used in practicing the present invention. Nor is the present invention limited in scope to single-chamber pacemakers. The present invention may also be practiced in connection with multiple-chamber (e.g., dual-chamber) pacemakers.

Figure 2:
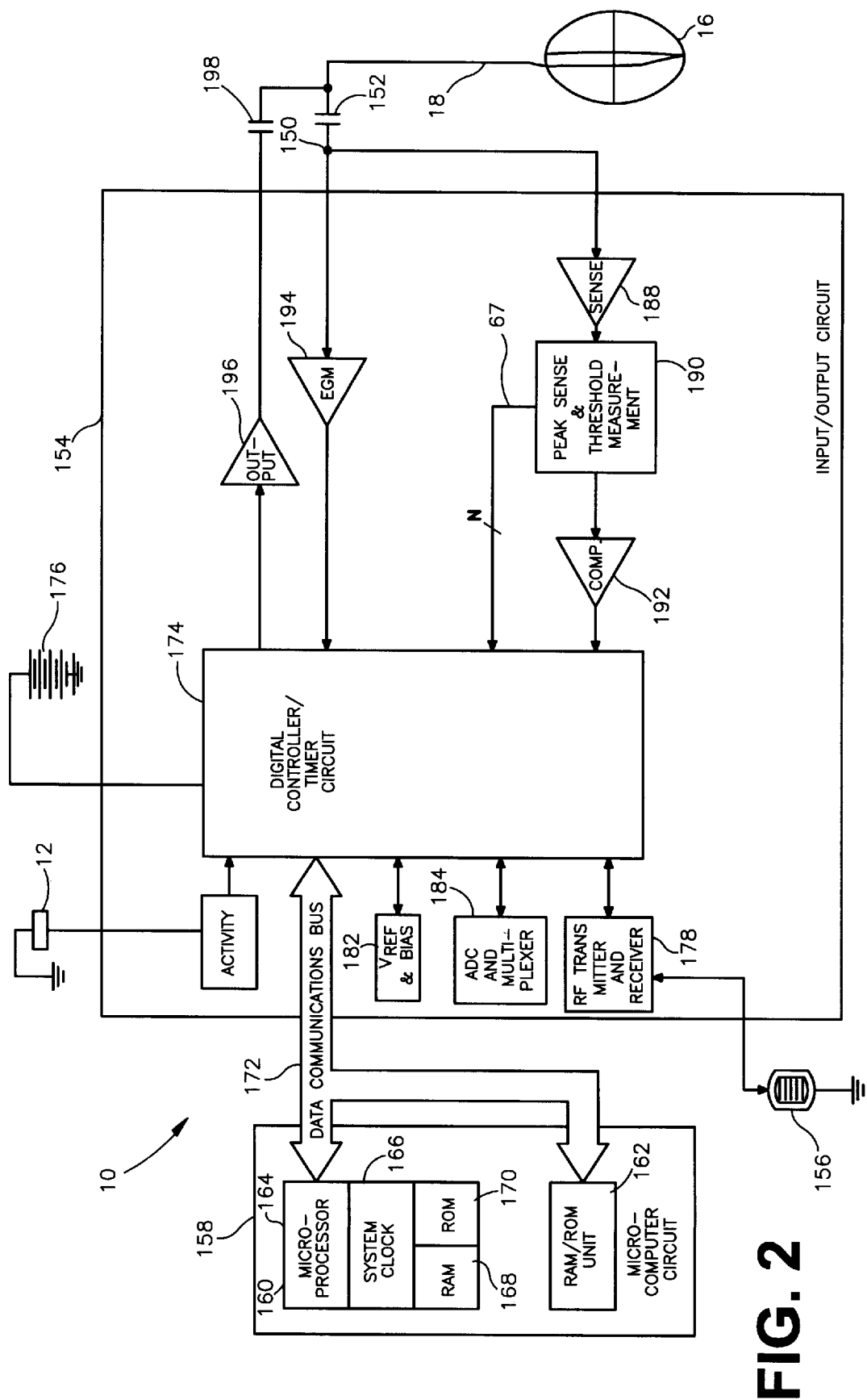
FIG. 2 shows a block diagram of a pacemaker in accordance with one disclosed embodiment of the present invention.

FIG. 2 shows a block diagram illustrating the constituent components of a pacemaker 10 in accordance with one embodiment of the present invention, where pacemaker 10 has a microprocessor-based architecture. The present invention may be utilized in conjunction with other implantable medical devices, however, such as cardioverters, defibrillators, cardiac assist systems, and the like, or in conjunction with other design architectures.

In the illustrative embodiment shown in FIGS. 1 and 2, pacemaker 10 includes an activity sensor 12, which is preferably a piezoceramic accelerometer bonded to the hybrid circuit inside the pacemaker housing. Piezoceramic accelerometer sensor 12 provides a sensor output which varies as a function of a measured parameter that relates to the metabolic requirements of patient.

Pacemaker 10 of FIG. 2 is most preferably programmable by means of an external programming unit (not shown in the Figures). One such programmer suitable for the purposes of the present invention is the commercially available Medtronic Model 9790 programmer. The programmer is a microprocessor device which provides a series of encoded signals to pacemaker 10 by means of a programming head which transmits radio-frequency (RF) encoded signals to pacemaker 10 according to a telemetry system such as that described in U.S. Pat. No. 5,312,453 to Wyborny et al., the disclosure of which is hereby incorporated by reference herein in its entirety. It is to be understood, however, that the programming methodology disclosed in Wyborny et al. patent is identified herein for the illustrative purposes only, and that any programming methodology may be employed so long as the desired information is transmitted to and from the pacemaker. One of skill in the art may choose from any of a number of available programming techniques to accomplish this task.

Pacemaker 10 is schematically shown in FIG. 2 to be electrically coupled to pacing lead 18 disposed in patient's heart 16. Lead 18 preferably includes an intracardiac electrode disposed at or near its distal end and positioned within the right ventricular (RV) or right atrial (RA) chamber of heart 16. Lead 18 may have unipolar or bipolar electrodes disposed thereon, as is well known in the art Although an application of the present invention in the context of a single-chamber pacemaker is disclosed herein for illustrative purposes, it is to be understood that the present invention may equally well be applied in the context of dual- or other multi-chamber pacemakers or implantable devices.

Lead 18 is coupled to a node 150 in the circuitry of pacemaker 10 through input capacitor 152. In the presently disclosed embodiment, accelerometer 12 is attached to the hybrid circuit inside pacemaker 10, and is not shown explicitly in FIG. 2. The output from accelerometer 12 is coupled to input/output circuit 154. Input/output circuit 154 contains analog circuits for interfacing to heart 16, accelerometer 12, antenna 156, and circuits for the application of stimulating pulses to heart 16 to control its rate under control of software-implemented algorithms in microcomputer circuit 158.

Microcomputer circuit 158 preferably comprises on-board circuit 160 and off-board circuit 162. Circuit 158 may correspond to the microcomputer circuit disclosed in U.S. Pat. No. 5,312,453 to Shelton et al.. the disclosure of which is hereby incorporated by reference herein in its entirety. On-board circuit 160 includes microprocessor 164, system clock circuit 166, and on-board RAM 168 and ROM 170. In the presently disclosed embodiment of the invention, off-board circuit 162 comprises a RAM/ROM unit. On-board circuit 160 and off-board circuit 162 are each coupled by a data communication bus 172 to a digital controller/timer circuit 174. Microcomputer circuit 158 may form a custom integrated circuit device augmented by standard RAM/ROM components.

The electrical components shown in FIG. 2 are powered by an appropriate implantable battery power source 176, in accordance with common practice in the art. For the sake of clarity, the coupling of battery power to the various components of pacemaker 10 is not shown in the Figures.

Antenna 156 is connected to input/output circuit 154 to permit uplink/downlink telemetry through RF transmitter and receiver unit 178. Unit 178 may correspond to the telemetry and program logic disclosed in U.S. Pat. No. 4,566,063 issued to Thompson et al., hereby incorporated by reference herein in its entirety, or to that disclosed in the above-referenced Wyborny et al. patent. The particular programming and telemetry scheme chosen is not believed to be critical for purposes of practicing the present invention so long as entry and storage of values of rate-response parameters are permitted.

$V_{REF}$ and Bias circuit 182 generates a stable voltage reference and bias currents for the analog circuits of input/output circuit 154. Analog-to-digital converter (ADC) and multiplexer unit 184 digitizes analog signals and voltages to provide "real-time" telemetry intracardiac signals and battery end-of-life (EOL) replacement function.

Operating commands for controlling the timing of pacemaker 10 are coupled by data bus 172 to digital controller/timer circuit 174, where digital timers and counters establish the overall escape interval of the pacemaker as well as various refractory, blanking and other timing windows for controlling the operation of the peripheral components disposed within input/output circuit 154.

Digital controller/timer circuit 174 is preferably coupled to sensing circuitry, including sense amplifier 188, peak sense and threshold measurement unit 190 and comparator/threshold detector 192. Circuit 174 is further preferably coupled to electrogram (EGM) amplifier 194 for receiving amplified and processed signals sensed by an electrode disposed on lead 18. Sense amplifier 188 amplifies sensed electrical cardiac signals and provides an amplified signal to peak sense and threshold measurement circuitry 190, which in turn provides an indication of peak sensed voltages and measured sense amplifier threshold voltages on multiple conductor signal path 67 to digital controller/timer circuit 174. An amplified sense amplifier signal is then provided to comparator/threshold detector 192. Sense amplifier 188 may correspond to that disclosed in U.S. Pat. No. 4,379,459 to Stein, which is hereby incorporated by reference herein in its entirety.

The electrogram signal provided by EGM amplifier 194 is employed when the implanted device is being interrogated by an external programmer (not shown) to transmit by uplink telemetric means a representation of an analog electrogram of the patient's electrical heart activity. See, for example, U.S. Pat. No. 4,556,063 to Thompson et al., hereby incorporated by reference herein in its entirety. Output pulse generator 196 provides pacing stimuli to patient's heart 16 through coupling capacitor 198 in response to a pacing trigger signal provided by digital controller/timer circuit 174 each time the escape interval times out, an externally transmitted pacing command is received, or in response to other stored commands as is well known in the pacing art. Output amplifier 196 may correspond generally to the output amplifier disclosed in U.S. Pat. No. 4,476,868 to Thompson, also incorporated by reference herein in its entirety.

While specific embodiments of input amplifier 188, output amplifier 196 and EGM amplifier 194 have been identified herein, this is done for the purposes of illustration only. The specific embodiments of such circuits are not critical to practicing the present invention so long as the circuits provide means for generating a stimulating pulse and are capable of providing digital controller/timer circuit 174 with signals indicative of natural or stimulated contractions of the heart.

Figure 3:
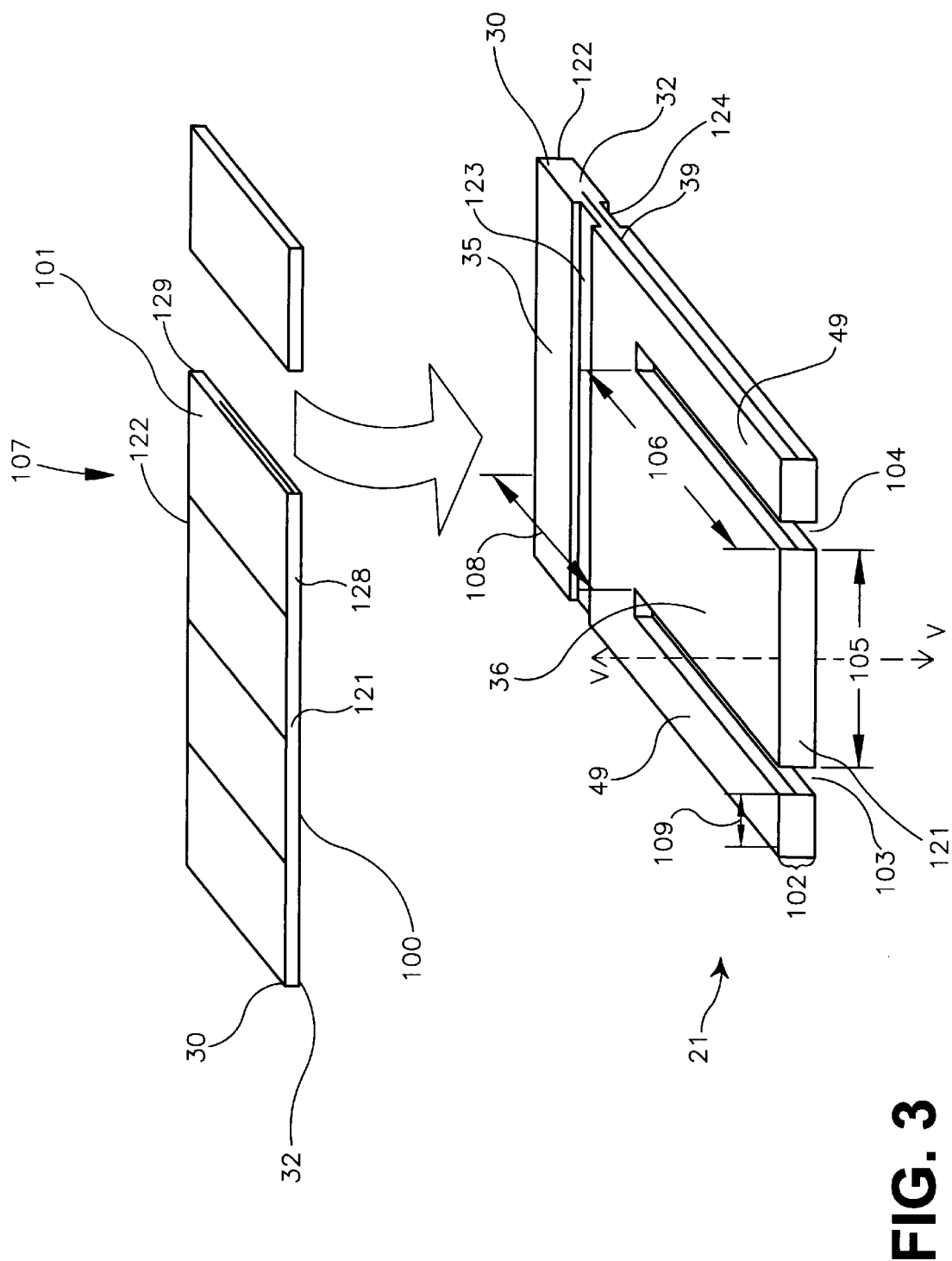
FIG. 3 schematically illustrates some steps according to one method of manufacturing an accelerometer component of the present invention.
Figure 4A:
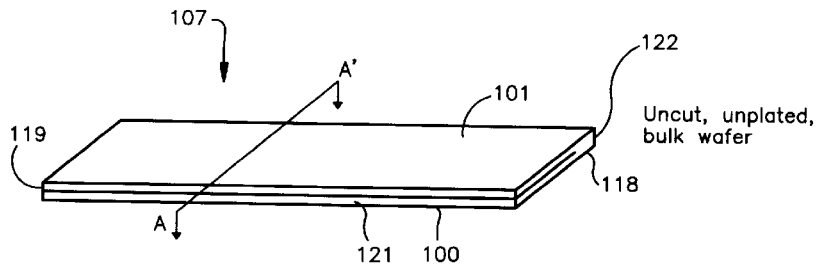
FIGS. 4(a) through 4(f) show diagrammatic representations of some steps corresponding to one method of manufacturing an accelerometer component of the present invention.
Figure 4B:
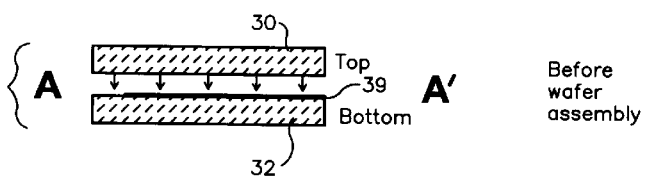
Figure 4C:
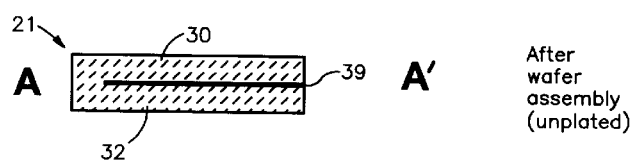
Figure 4D:
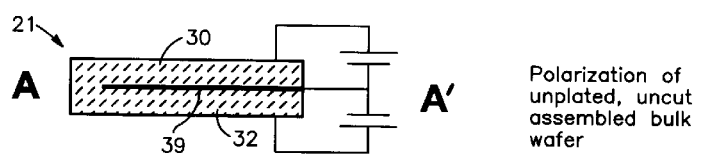
Figure 4E:
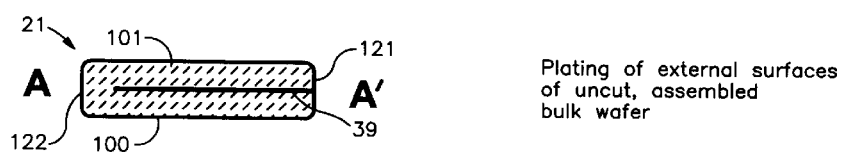
Figure 4F:
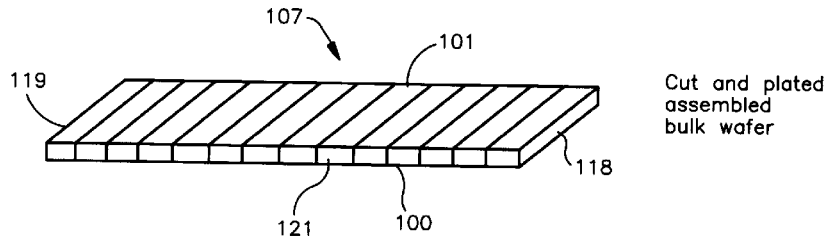

FIGS. 3 and 4(*a*) through 4(*f*) schematically illustrate some steps according to several methods of manufacturing piezoelectric sub-assembly 21 of accelerometer assembly 12 of the present invention. In FIGS. 3 and 4(*a*) through 4(*f*), upper and lower sheets 30 and 32 comprise a piezoelectric material such as lead zirconate titanate, quartz, lithium niobate, lithium titanate or any other suitable material having the desired piezoelectric properties. Sheets 30 and 32 may each be formed from multiple layers of tape, or may alternatively each form a single monolithic layer formed from, for example, granules of suitable piezoelectric material that are subsequently compressed together.

As shown in FIGS. 4(*b*) and 4(*c*), sheets 30 and 32 are bonded together to form a multi-layer structure, and are separated by interposing intermediate metallization layer or plating 39. Metallization layer 39 is most preferably formed of printed or deposited platinum paste, but may be formed from pastes comprising metals other than platinum such as tungsten, molybdenum, osmium, iridium, technetium, rhenium, rhodium and ruthenium, and alloys, mixtures and combinations thereof.

Sheets 30 and 32 are most preferably formed of green ceramic tape upon one of the internal surfaces of which intermediate layer 39 is printed or deposited, most preferably as a thick film comprising platinum, but less preferably as a thick film or thin film comprising other suitable metals or alloys. The resulting laminated structure comprising sheets 30 and 32 formed of unfired green ceramic tape and thick film platinum layer 39 is then most preferably co-fired at temperatures approximating 1,000 degrees Celsius for an appropriate period of time and in a suitable atmosphere, thereby producing a fired sub-assembly.

In a preferred embodiment of the present invention, layer 39 does not extend completely between front edge 128 and rear edge 129 between sheets 30 and 32, but instead originates near or at front edge 128 and terminates a short distance before reaching rear edge 129.

As illustrated in FIG. 4(*d*), upper and lower sheets 30 and 32 of piezoelectric sheet 107 are electrically "poled" or polarized in appropriate orientations by known conventional means to yield a sheet having the desired piezoelectric properties. That is, the respective orientations of the principal electrical axes corresponding to upper and lower sheets 30 and 32 are defined during a "poling" or polarizing step. FIGS. 3 and 4(*f*) show how sheet 107 is then cut into smaller rectangular elements, usually with a ceramic cutting saw. More information concerning piezoelectric ceramic devices and methods of manufacturing same may be found in the "Guide to Modern Piezoelectric Ceramics," Rev. 3-93, pp. 1–27, published by Morgan Matroc, Electro Ceramics Division, Bedford, Ohio, and the various technical references cited therein, all of which publications are hereby incorporated by reference herein in their respective entireties.

Next, and as illustrated in FIG. 4(*e*), external electrically conductive layers 100 and 101 are deposited or plated, most preferably by an electroless plating process, on the upper and lower surfaces of sheet 107. External electrically conductive layers 121 and 122 are also deposited or plated (also most preferably by an electroless plating process) on ends 128 and 129 of sheet 107, thereby resulting in upper and lower surfaces of sheet 107 being electrically continuous respecting one another. In preferred methods of the present invention, layers 100, 101, 118, 119, 121 and 122 of sheet 107 are deposited or plated simultaneously using an electroless plating process; layers 118 and 119 appear on two opposing ends of sheet 107 and are discarded when sheet 107 is cut into individual piezoelectric subassemblies 21.

Layers 100, 101, 121 and 122 are most preferably formed of nickel, but may also be formed from any other suitable electrically conductive metal or material other than nickel, such as at least one metal selected from the group consisting of gold, silver, tungsten, molybdenum, palladium, platinum, osmium, iridium, technetium, rhenium, rhodium and ruthenium, and alloys, mixtures and combinations thereof. Layers 100, 101, 121 and 122 may also be deposited, plated or emplaced on the various external surfaces of sheet 107 by means other than electroless plating. Finally, the electrically conductive areas defined by layers 100, 101, 121 and 122 need not assume the form of layers that continuously cover all or even most portions of the top, bottom and side surfaces of sheet 107, but instead may assume any of a number of different geometric configurations such as strips, irregularly shaped areas, zigzags and the like.

Electrically isolating strips, notches or areas 123 and 124 of FIG. 3 are next defined in any of a number of different suitable ways and configurations to separate electrically and isolate electrically various portions of electrically conductive layers 100, 101, 121, 122 and 39 from one another. For example, electrically isolating strips 123 and 124 may be formed by cutting notches through layers 100 and 101 by laser scribing or diamond bladed wheel cutting means. Alternatively, electrically isolating strips 123 and 124 may be formed by photo-etching or acid etching means. Electrically isolating strips 123 and 124 may also be formed by masking suitable locations of the various surfaces of sheet 107 wit a plating resist material prior to an external surface plating or electrodeposition step to prevent the formation of electrically conductive metal layer thereon, and thereby provide electrical isolation between certain portions of electrically conductive layers 100, 101, 121, 122 and 39. Various embodiments of the present invention include piezoelectric sub-assemblies having only one, only two, or three or more electrically isolating strips or areas disposed on the external surfaces thereof which interrupt the electrical continuity between certain portions of electrically conductive layers 100, 101, 121, 122 and 39.

In one embodiment of the present invention, the step of defining active area 36 (the cantilever beam) and inactive area 35 (which couples piezoelectric accelerometer 12 to a hybrid circuit) shown in FIG. 3 is performed by using a diamond bladed wheel to cut notches 103 and 104. Incisions or notches 103 and 104 separate inactive and active areas of accelerometer 12. Incisions or notches 103 and 104 in piezoelectric sub-assembly 21 also define the sensitivity of the resulting accelerometer by controlling beam width 105 and length 106.

FIG. 5 illustrates one manner in which an assembled medical device such as a cardiac pacemaker may be formed by mounting one or more feedthroughs 509 to shields 505 and 507. Internal electronics such as pulse generator circuitry, accelerometer assembly 12 and battery or electrochemical cell 503 are disposed within shields 505 and 507. Battery 503 is coupled to circuitry through additional feedthroughs that are not shown in the Figures. Shields 505 and 507 are preferably laser welded together along their edges to form an hermetic enclosure. A molded plastic connector block assembly (not shown in the Figures) containing electrical connectors for attachment of medical leads to feedthroughs 509 is typically installed atop shields 505 and 507 sometime thereafter.

In FIG. 5, accelerometer assembly 12 most preferably permits direct attachment thereof to a hybrid circuit. Accelerometer assembly 12 is preferably attached to such a circuit by solder reflow or conductive epoxy film or adhesive means. Such means provide an electrical connection to bottom electrode 44 of accelerometer assembly 12 and elevate accelerometer assembly 12 from the hybrid substrate surface. Furthermore, the attachment process described above substantially reduces or eliminates the variability of the electrical output signal provided by sub-assembly 21 through the provision of a consistent, reliable means for attaching accelerometer assembly 12 to the pacemaker hybrid. The amplitude of the electrical output signal of sub-assembly 21 may also be adjusted by reducing the amount of metallization disposed on the top or bottom portions of beam 36 using conventional laser trimming means to reduce the effective net length thereof.

FIGS. 6(*a*) and 6(*b*) show top and side views, respectively, of cut and plated piezoelectric sub-assembly 21 prior to the formation of electrical isolation areas thereon by cutting, laser scribe or other means. External electrically conductive layers 101, 102, 121 and 122 most preferably surround all portions of wafer 107 except for side surfaces 126 and 127. Alternatively, and as discussed above, external electrically conductive layers 101, 102, 121 and 122 may be disposed only on at least some of the external surfaces of wafer 107. Electrically conductive intermediate layer 39 is electrically connected to front edge layer 121, and most preferably terminates prior to reaching or being electrically connected to rear edge layer 122.

FIGS. 7(*a*) through 7(*c*) show piezoelectric sub-assembly 21 of FIGS. 6(*a*) and 6(*b*) after it has been and electrically and mechanically connected to electrical connections A and B, and subjected to laser scribing or cutting steps for forming electrical isolation areas 123, 124, and 125. At least portions of the external electrically conductive layers are electrically isolated from one another by electrical isolation areas or strips 123, 124 and 125. FIG. 7(*d*) illustrates schematically the electrical configuration of sub-assembly 21 of FIGS. 7(*a*) through 7(*c*). FIG. 7(*d*) shows that sub-assembly 21 of FIGS. 7(*a*) through 7(*c*) provides a sensor having the capacitive elements thereof arranged electrically in series. It is well known that two capacitive elements arranged in series provide a total capacitance which is equal to one-half the sum of the individual capacitive elements. Thus, the total capacitance of sub-assembly 21 illustrated in FIGS. 8(*a*) through 8(*c*), where $C_1C_2=C$, equals (½)C. Such an electrical configuration may find application in circumstances where higher output voltages (as opposed to higher charge outputs) are desired.

FIGS. 8(*a*) through 8(*c*) show piezoelectric sub-assembly 21 of FIGS. 6(*a*) and 6(*b*) after it has been electrically and mechanically connected to electrical connections A and B, and subjected to laser scribing or cutting steps for forming electrical isolation areas 123 and 124. FIG. 8(*d*) illustrates schematically the electrical configuration of sub-assembly 21 of FIGS. 8(*a*) through 8(*c*). FIG. 8(*d*) shows that sub-assembly 21 of FIGS. 8(*a*) through 8(*c*) provides a sensor having the capacitive elements thereof arranged electrically in parallel. It is well known that capacitive elements arranged in parallel provide a total capacitance which is the sum of the individual capacitive elements. Thus, the total capacitance of sub-assembly 21 illustrated in FIGS. 8(*a*) through 8(*c*), where $C_1=C_2=C$, equals 2C. Because the output provided by a piezoelectric sensor having capacitive elements is generally directly proportional to the total capacitance of the sensor, the output provided by the sensor is approximately twice that of an otherwise similar conventional piezoelectric sensor. (The output provided by a piezoelectric sensor is proportional to the charge provided by the sensor. Charge—or Q—in turn, equals CV.)

FIGS. 9(*a*) through 9(*d*) show selected views of one embodiment of piezoelectric sub-assembly 21 of the present invention, such embodiment being largely similar to sub-assembly 21 shown in FIGS. 8(*a*) through 8(*c*). Notches 103 and 104 are formed therein, however, to provide a central cantilever beam having active area 36.

FIG. 10(*a*) shows a side view of accelerometer assembly 12 incorporating piezoelectric sub-assembly 21 of FIGS. 9(*a*) through 9(*d*) therein. FIG. 10(*b*) shows a front view of accelerometer assembly 12 incorporating piezoelectric sub-assembly 21 of FIGS. 9(*a*) through 9(*d*) therein. Accelerometer assembly 12 of FIGS. 10(*a*) and 10(*b*) is configured such that the two capacitive elements of subassembly 21 are arranged electrically in parallel respecting one another. As shown in FIGS. 10(*a*) and 10(*b*), electrically non-conductive epoxy 48 is most preferably disposed between upper member 61 and the top surface of sub-assembly 21, and between lower member 41 and the bottom surface of sub-assembly 21. Electrically conductive contacts 51 and 52, most preferably formed from gold plating, are disposed on upper member 61 and lower member 41, respectively, such that appropriate electrical and mechanical connections are established between appropriate portions of sub-assembly 21 and electrical connections A and B. FIG. 10(c) illustrates schematically the electrical configuration of accelerometer assembly 12 of FIGS. 10(a) and 10(b), where the two capacitive elements of subassembly 21 are arranged electrically in parallel respecting one another.

Figure 11A:
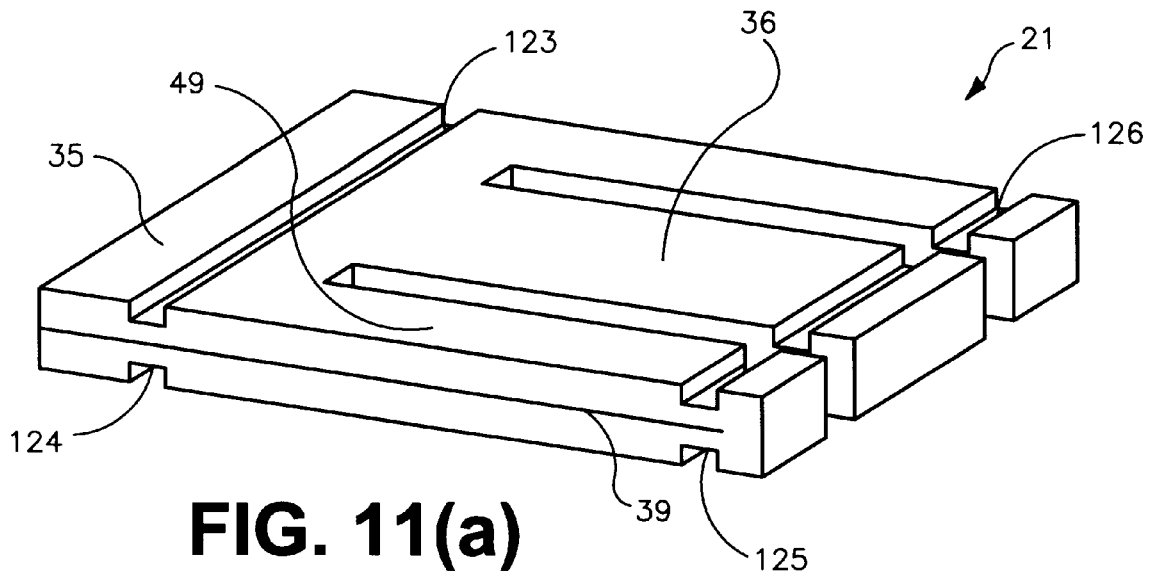
FIGS. 11(a) through 11(c) show selected views of another embodiment of piezoelectric sub-assembly 21 of the present invention.
Figure 11B:
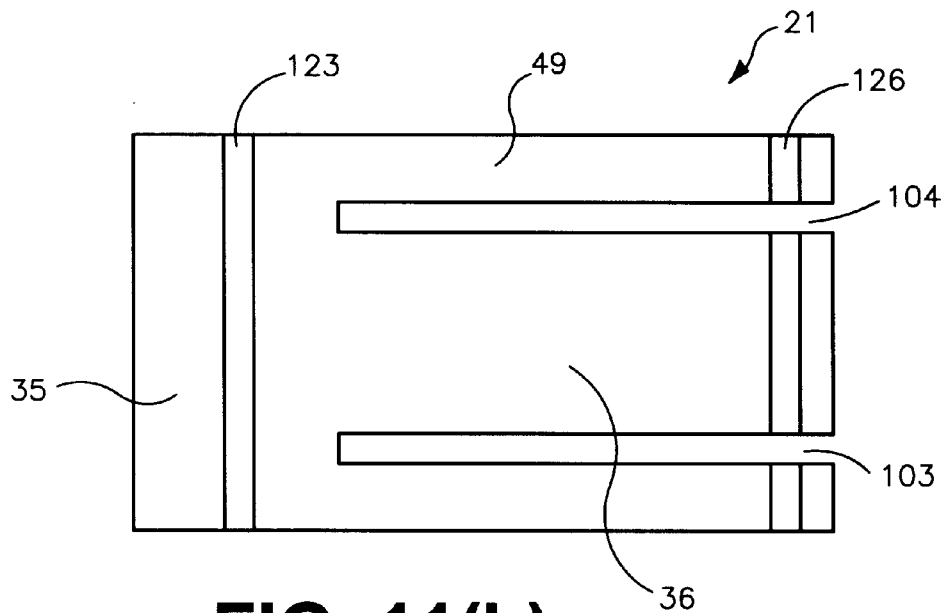
Figure 11C:
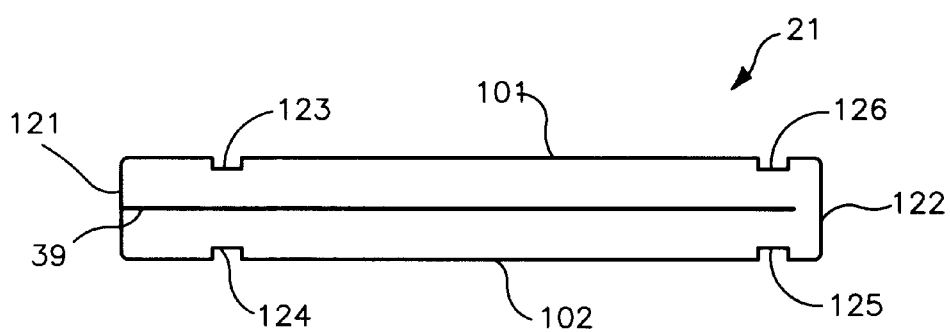

FIGS. 11(a) through 11(c) show selected views of another embodiment of piezoelectric sub-assembly 21 of the present invention. In this embodiment of the present invention, four electrical isolation areas forming strips are disposed on the top and bottom surfaces of piezoelectric sub-assembly 21. Active area 35 is defined approximately by a central cantilever beam. FIGS. 12(a) through 12(c) show selected views of an accelerometer assembly having piezoelectric subassembly 21 of FIGS. 11(a) through 11(c) disposed therein, where FIG. 12(a) presents a side view thereof, FIG. 12(b) shows a bottom view thereof and FIG. 12(c) shows a top view thereof. Electrical contacts A and B are electrically connected to appropriate portions of sub-assembly 21 by gold or other electrically conductive plating or epoxy 51, 52 and 53. Electrically non-conductive epoxy 48 is most preferably disposed between upper member 61 and the top surface of sub-assembly 21, and between lower member 41 and the bottom surface of sub-assembly 21. FIG. 12(c) shows that accelerometer assembly 12 may be attached to a hybrid circuit easily owing to electrical contacts A and B being exposed and present on the same surface of assembly 12. FIG. 12(d) illustrates schematically the electrical configuration of accelerometer assembly 12 of FIGS. 12(a) through 12(c), where the two capacitive elements of sub-assembly 21 are arranged electrically in parallel respecting one another.

FIGS. 13(a) through 13(f) show selected views and preferred dimensions of one embodiment of accelerometer assembly 12 of the present invention. FIGS. 14(a) through 14(c) show other views of the accelerometer assembly of FIGS. 13(a) through 13(f). Some preferred dimensions for piezoelectric sub-assembly 21 in FIGS. 13(a) through 13((f) are about 0.133 inches for length 106 of notches 103 and 104; about 0.010 inches for the width 113 of notch 103 or 104; about 0.080 inches for width 105 of beam 36; about 0.025 inches for width 109 of arms 49; about 0.014 inches for overall thickness 102 of accelerometer 12; and about 0.047 inches for length 108 of inactive area 35.

In preferred embodiments of the present invention, substantially vertical deflection of beam 35 along imaginary axis V is limited to distances not exceeding about 0.002 inches through the action of stop 70 shown in FIGS. 13(d) through 14(c). Even more preferably, substantially vertical deflection of beam 35 along imaginary axis V is limited to distances not exceeding about 0.0005 inches through the action of stop 70. FIGS. 13(a) through 13(e) show further preferred dimensions for most of the components comprising one preferred embodiment of accelerometer assembly 12. Of course, dimensions and beam deflection ranges other than those set forth explicitly herein are also contemplated in the present invention.

ENDEVCO™ of San Juan Capistrano, Calif. and MORGAN COMPANY™ of Bedford, Ohio supply suitable materials for forming accelerometer assemblies 12 of the present invention. Both companies may also be capable of providing machined and formed accelerometer assemblies 12 and piezoelectric subassemblies 21 of the present invention.

FIGS. 13(a) through 14(c) show the components required to form one embodiment of accelerometer assembly 12 of the present invention. Lower component 41, piezoelectric sub-assembly 21, upper component 61, conductive thermoplastic or epoxy 47 and stop 70 are preferably configured and assembled as shown in those Figures. Upper housing member 61 most preferably assumes the same shape and structure as lower housing member 41, but is oriented to face lower housing member 41 such that downwardly extending arms 62 of upper housing member 61 align with upwardly extending arms 42 of lower housing member 41.

Stops 70 of upper and lower housing members 61 and 41 limit the vertical range of motion of beam 35 when beam 35 defects in response to being subjected to a suitably great force or acceleration. By limiting the vertical range of motion through which beam 35 may move, stops 70 prevent beam 35 from failing or fracturing as a result of excessive deflection. Stops 70 may be incorporated into upper housing member 61 alone, lower housing member 41 alone, or most preferably into both upper and lower housing members 61 and 41.

Upper and lower housing members 41 and 61 are most preferably formed from blocks of Kovar or Alloy 42, where the blocks are chemically etched to provide the desired structural shape and outlines of those members, followed by nickel-gold alloy plating of the exterior surfaces thereof to reduce or eliminate oxidation. Kovar and Alloy 42 have been found to provide the advantages of being structurally robust, inexpensive, chemically etchable and platable with alloys or metals for preventing oxidation. NORTHWEST ETCH TECHNOLOGY™ of Tacoma, Wash. provides Kovar etching services suitable for practicing the present invention. JOHNSON MATTHEY, INC.™ of Washington State provides nickel-gold alloy plating services suitable for practicing the present invention.

Other materials such as copper, aluminum, brass, nickel, platinum and other noble metals, and conductive carbon composites, suitable ceramic compositions or plastic capable of accepting metallic plating on the exterior surfaces thereof, may be employed to form upper and lower housing members 41 and 61. Upper and lower housing members 41 and 61 may also be machined, milled or stamped from blocks of suitable material.

Outer members 49 of piezoelectric sub-assembly 21 are employed to mount sub-assembly 21 within a low cost protective package in accordance with a preferred embodiment of the present invention. In FIGS. 14(a) through 14(c), lower housing member 41 preferably assumes "W" shaped cross-section 43 to permit suitable vertical movement of beam 36. Lower housing member 41 and upper housing member 61 are most preferably formed to contact only outer arms or members 49. Electrically conductive material 47 is disposed on at least portions of the upper surfaces of upwardly extending arms 42 and the lower surfaces of downwardly extending arms 62 before sub-assembly 21 is mounted and sandwiched therebetween.

Electrically conductive material 47 may comprise any of a number of materials such as a suitable electrically conductive epoxy or other glue. Electrically conductive material 47 most preferably comprises a thermoplastic such as STAY-STIK™ 181 silver-filled paste manufactured by ALPHA METALS™ of Jersey City, N.J. In a preferred embodiment of the present invention, material 47 is a STAYSTIK wet paste formulation containing a resin and a diluent that is applied, respectively, onto the top and bottom surfaces of upwardly extending arms 42 and downwardly extending arms 62 by a conventional screening process employing a metal stencil. Such a wet paste formulation is preferably laid down on those top and bottom surfaces in layers about 0.005 inches thick. Upper and lower housing members 61 and 41 containing the so-applied paste are then dried in an oven containing a nitrogen atmosphere at temperatures ranging between about 200 degrees F. and about 300 degrees F. for periods of time ranging between about 45 minutes and about 90 minutes.

Following drying of the thermoplastic, lower housing member 41 is placed in a tool, sub-assembly 21 is placed atop lower housing member 41, and upper housing member 61 is placed atop sub-assembly 21 such that outward arms 49 of accelerometer 12 are sandwiched or interposed between upwardly extending arms 42 of lower housing member 41 and downwardly extending arms 62 of upper housing member 61. Material 47 forms an electrical connection and mechanical bond between the upper metal plated surfaces of upwardly extending arms 42 of lower housing member 41, the lower metal-plated surfaces of downwardly extending arms 62 of upper housing member 61, and upper and lower housing members 61 and 41. A compression spring applying between about 8 and about 24 ounces of force is then positioned accelerometer assembly 12, and assembly 12 and the spring are placed in an oven containing a nitrogen atmosphere having a temperature of about 400 degrees F. for about 60 minutes. Assembly 12 is then removed from the oven and permitted to cool.

Accelerometer assembly 12 is preferably tested and characterized prior to coupling first terminal 44 of assembly 12 with lead/tin solder to a hybrid (not shown in FIGS. 14(a) through 14(c)) and coupling by ultrasonic wire bonding means second terminal 64 to the hybrid by an aluminum or gold wire bond.

The protective packaging process of the present invention enhances manufacturing yields by reducing or eliminating variability in the amplitude of the output signal to thereby provide a consistent, reliable means for attaching piezoelectric sub-assembly 21 to the protective package defined by assembly 12. Moreover, the output signal provided by assembly 12 may be increased by mechanically biasing sensor base 35 of piezoelectric sub-assembly 21 during the accelerometer assembly forming process.

The manner in which outer members 49 of sub-assembly 21 are bonded to upper and lower housing members 61 and 41 may also add to or diminish the amplitude of the output signal provided by assembly 12. For example, if electrically conductive thermoplastic or epoxy is applied from a point near or on base 35 of subassembly 21 to a point near the opposite end of sub-assembly 21 along outer members 49, movement of sub-assembly 21 in the region defined by base 35 is diminished, and hence the overall output signal provided by sub-assembly 21 is increased in amplitude. As the amount of material 47 applied to the region near base 35 decreases, movement of sub-assembly 12 in the region defined by base 35 increases, thereby decreasing the amplitude of the output signal provided by subassembly 21.

Figure 15A:
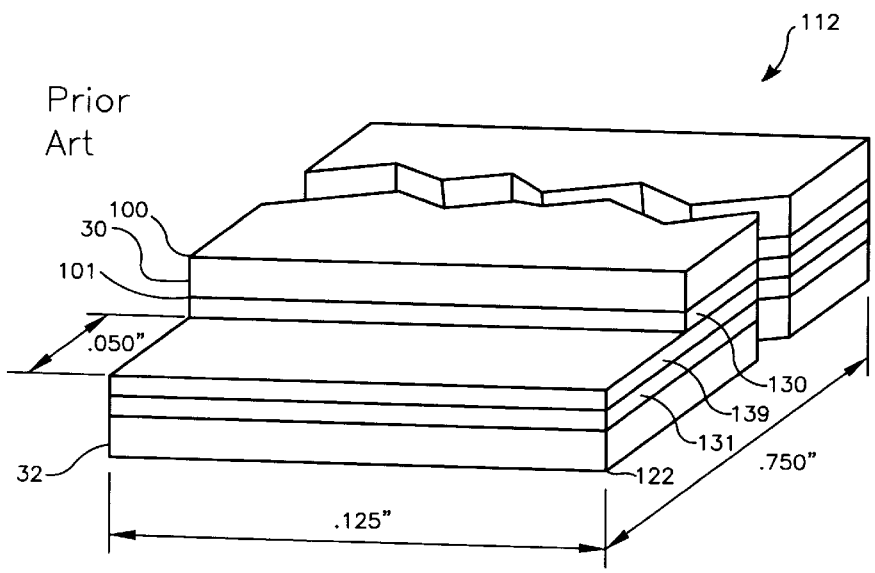
FIGS. 15(a) and 15(b) show selected views of a prior art piezoelectric sensor.
Figure 15B:
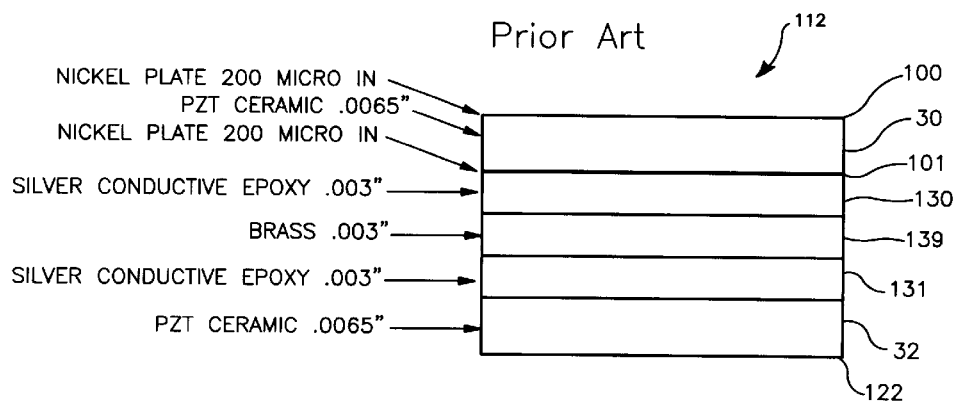

FIGS. 15(a) and 15(b) show selected views of a prior art piezoelectric sensor of the monopole flexural type. FIG. 15(a) shows a cut-away perspective view of monopole sensor assembly 112. FIG. 15(b) shows a cross-sectional view of monopole sensor assembly 112. Monopole sensor assembly 112 comprises upper and lower sheets 30 and 32 formed of a piezoelectric material such as lead zirconate titanate, quartz, lithium niobate, lithium titanate or any other suitable material having the desired piezoelectric properties. Sheets 30 and 32 may each be formed from multiple layers of tape, or may alternatively each form a single monolithic layer formed from, for example, granules of suitable piezoelectric material that have been compressed together. Sheet 30 has nickel plating layers 100 and 101 disposed on the upper and lower surfaces thereof. Those nickel plating layers are not contiguous with or physically connected to one another directly.

As shown in FIGS. 15(a) and 15(b), sheets 30 and 32 are bonded together to form a multi-layer monopole structure, and are separated by a plurality of interposing layers, including brass layer or plating 139. Layer 139 is most preferably formed of plated brass, but may be formed from other metals or electrically conductive materials such as platinum. Layers of electrically conductive silver epoxy 130 and 131 are disposed between and attach the top and bottom surfaces of brass layer 39 to upper and lower sheets 30 and 32. The resulting monopole structure must be subjected to a "poling" or polarization process where layer 30 is appropriately polarized for sensor 12 to be rendered operational for purposes of sensing patient activity.

Electrical connections for sensing patient activity are established to nickel plating layer 100 and brass layer 139 across layer 30 by electrical connections A and B, respectively. Layer 32 provides electrical insulation and isolation between shield, case or housing 14 of implantable medical device 10 and layer 30. Layer 32, in turn, is preferably attached to case or housing 14 by adhesive or glue 122, which most preferably is BLACK MAX™ cyanoacrylate adhesive.

Figure 16:
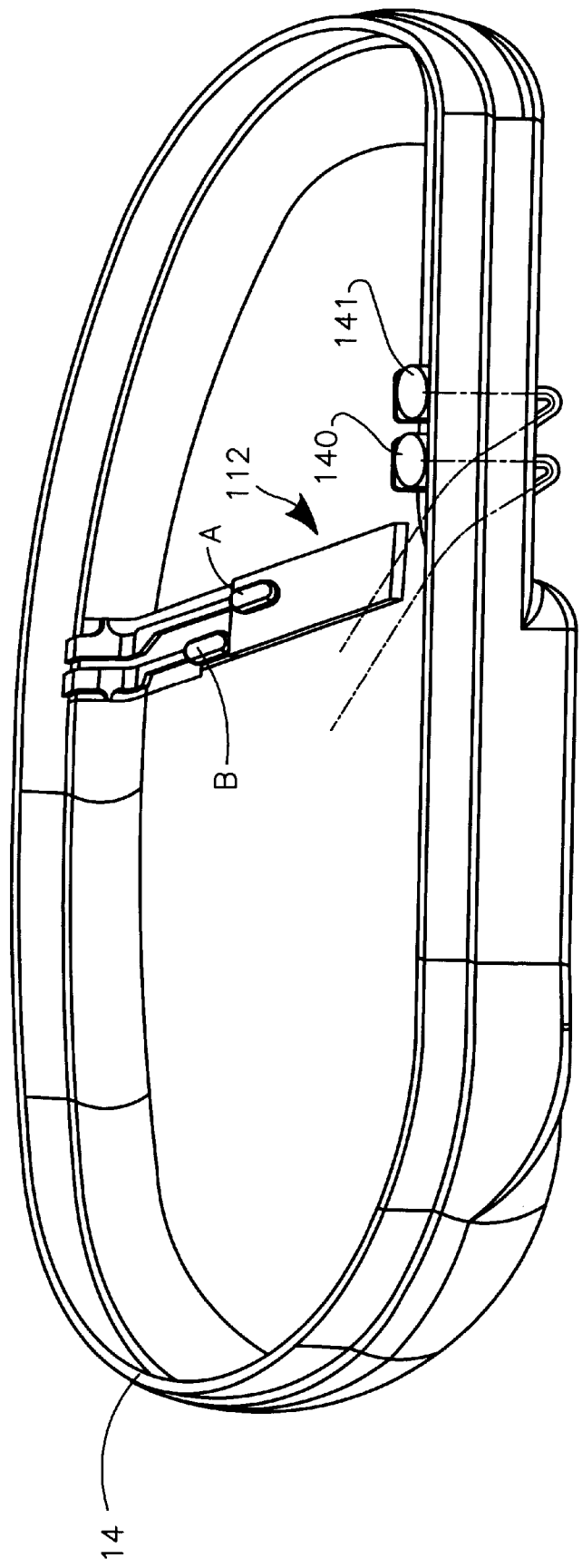
FIG. 16 shows the prior art piezoelectric sensor of FIGS. 15(a) and 15(b) mounted within and attached to the internal surface of a pacemaker shield.

FIG. 16 shows prior art sensor 112 of FIGS. 15(a) and 15(b) mounted within and attached to the internal surface of pacemaker shield or housing 14 of pacemaker 10. Feedthroughs 140 and 141 extend from the interior of housing 14 to the exterior thereof, and permit electrical leads 18 to be connected electrically to the electronic circuitry disposed within housing 14. First and second electrical connections A and B, respectively, are established to nickel plating layer 100 and brass layer 139, respectively.

Figure 17A:
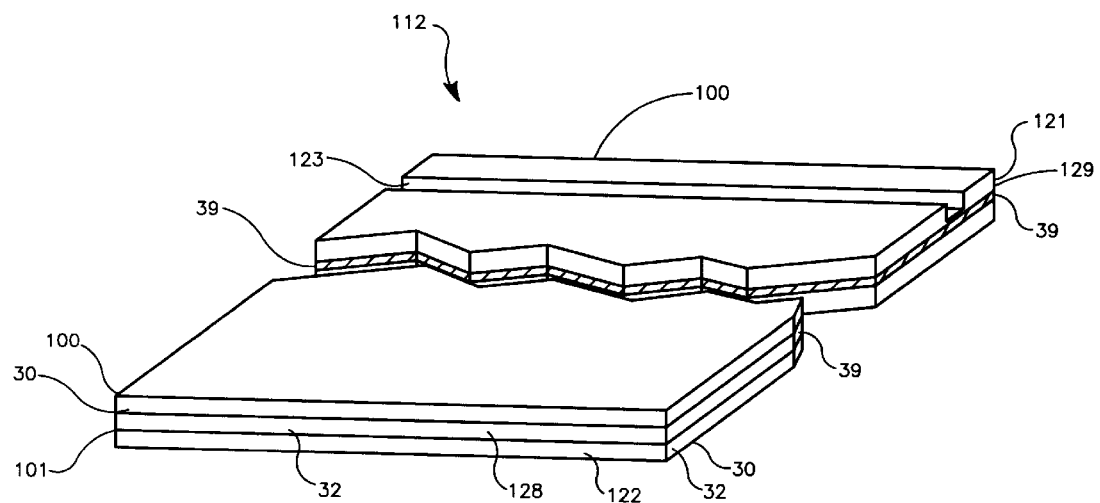
FIGS. 17(a) and 17(b) show selected views of an embodiment of a sensor of the present invention.
Figure 17B:
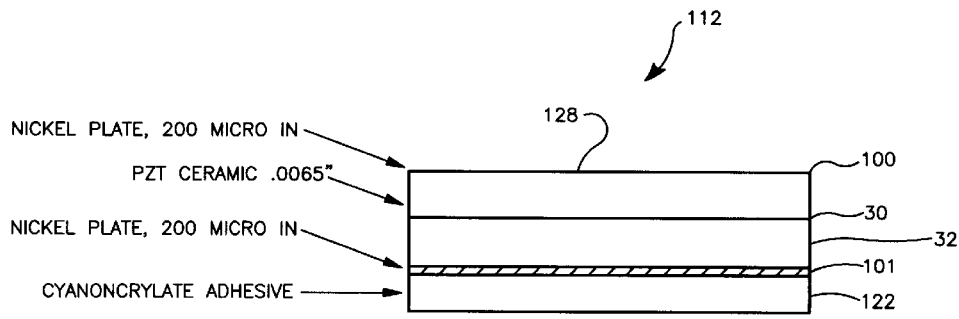

FIGS. 17(a) and 17(b) show selected views of one embodiment of a bipolar sensor of the present invention. FIG. 17(a) shows a cut-away perspective view of the top and front surfaces of bipolar sensor assembly 112.

FIG. 17(b) shows a cross-sectional view of the front edge of bipolar sensor assembly 112. Sensor assembly 112 comprises sheets 30 and 32 formed of a piezoelectric material such as lead zirconate titanate, quartz, lithium niobate, lithium titanate or any other suitable material having the desired piezoelectric properties. Sheets 30 and 32 may be formed from layers of tape, or may alternatively comprise layers formed from, for example, granules of suitable piezoelectric material that have been compressed together.

Sheet 30 has nickel plating layer 100 disposed on the top surface thereof. Sheet 32 has nickel plating layer 101 disposed on the lower surface thereof. Nickel plating layers 100 and 101 are made contiguous with and physically connected to one another by side or rear nickel plating layer 121 disposed on rear edge 129 of sensor 112. In a preferred embodiment of the present invention, no nickel plating layer is disposed on front edge 128 of sensor assembly 112. External layers 100 and 101 may be formed of other suitable metals or alloys other than silver, such as tungsten, gold, platinum, osmium, ruthenium, rhenium and the like.

Sheets 30 and 32 are bonded together to form a multilayer structure, and are separated by interposing intermediate metallization layer or plating 39. Metallization layer 39 is most preferably formed of printed or deposited platinum paste, but may be formed from pastes comprising metals other than platinum such as tungsten, molybdenum, osmium, iridium, technetium, rhenium, rhodium and ruthenium, and alloys, mixtures and combinations thereof.

Sheets 30 and 32 are most preferably formed of green ceramic tape, upon one of the internal surfaces of which intermediate layer 39 is printed or deposited, most preferably as a thick film comprising platinum, but less preferably as a thick film or thin film comprising other suitable metals or alloys. The resulting laminated structure comprising sheets 30 and 32 formed of unfired green ceramic tape and thick film platinum layer 39 is then most preferably co-fired at temperatures approximating 1,000 degrees Celsius for an appropriate period of time and in a suitable atmosphere, thereby producing a fired sub-assembly.

In a preferred embodiment of the present invention, layer 39 does not extend completely between front edge 128 and rear edge 129 between sheets 30 and 32, but instead originates near or at front edge 128 and terminates a short distance before reaching rear edge 129.

Upper and lower sheets 30 and 32 of piezoelectric sheet 107 are electrically "poled" or polarized in appropriate orientations by known conventional means to yield a sheet having the desired piezoelectric properties. That is, the respective orientations of the principal electrical axes corresponding to upper and lower sheets 30 and 32 are defined during a "poling" or polarizing step.

Electrically isolating strip, notch or area 123 shown in FIG. 17(a) may be defined in any of a number of different suitable ways and configurations to separate electrically and isolate electrically various portions of electrically conductive layers 100, 101, 121 and 39 from one another. In all embodiments of the present invention, strip, notch or area 123 is most preferably formed after sheets 30 and 32 have been poled or polarized. Various embodiments of the sensor of the present invention include piezoelectric sub-assemblies having only one, only two, or three or more electrically isolating strips or areas disposed on the external surfaces thereof which interrupt electrical continuity between certain portions of electrically conductive layers 100, 101, 121 and 39.

As shown in FIGS. 17(a) and 17(b), sheets 30 and 32 are bonded together to form a multi-layer bipolar structure, and are separated at least partially by intermediate metallization layer 39. Adhesive layer 122 provides electrical insulation and isolation between shield, case or housing 14 of implantable medical device 10 and sheet 32. Adhesive layer 122 is most preferably an electrically insulative adhesive or glue such as BLACK MAX™ cyanoacrylate adhesive, and may also include a suitable layer of electrically insulative woven or fibrous material, or a film such as polyimide.

Figure 18:
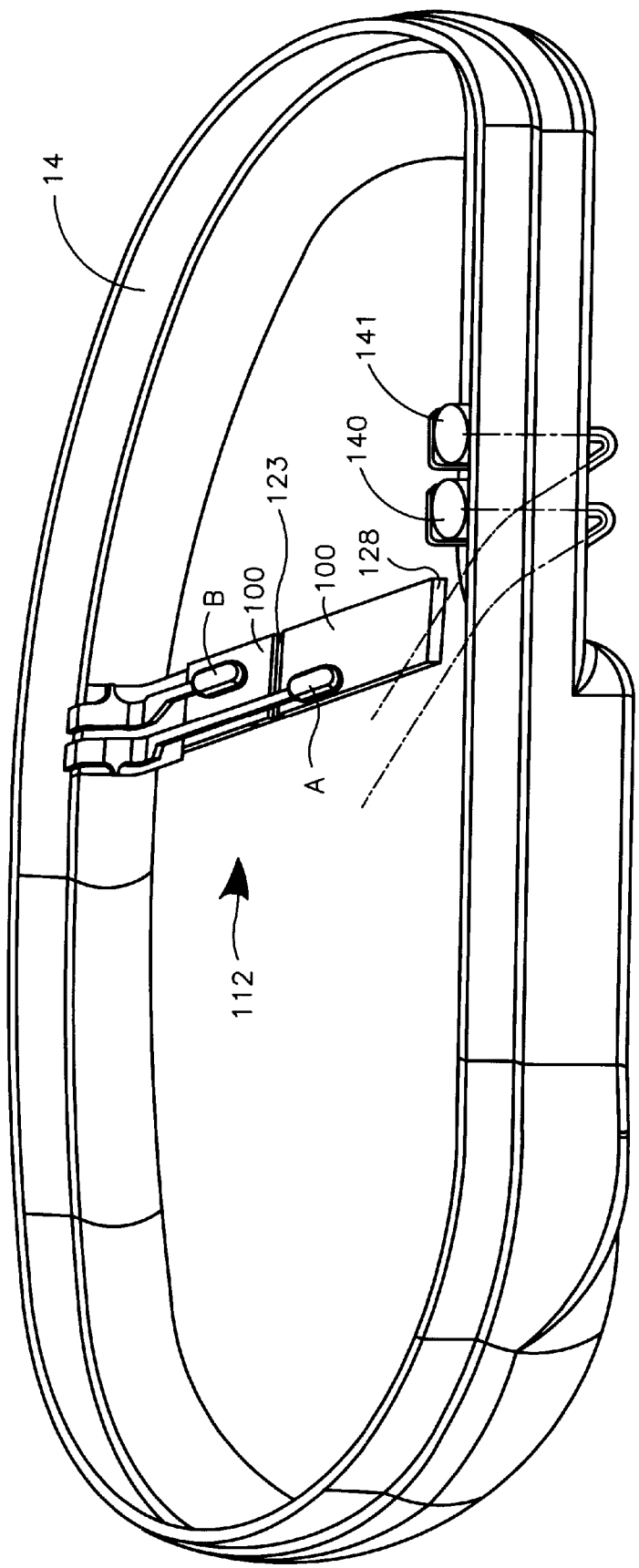
FIG. 18 shows the sensor of FIGS. 17(a) and 17(b) mounted within and attached to the internal surface of a pacemaker shield.

FIG. 18 shows bipolar sensor 112 of FIGS. 17(a) and 17(b) mounted within and attached to the internal surface of pacemaker shield or housing 14 of pacemaker 10. As shown in FIG. 18, electrical connections A and B for sensing patient activity are most preferably established first to a portion of nickel plating layer 100 disposed forwardly of notch 123, and second to a portion of nickel plating layer 100 disposed rearwardly of notch 123. Feedthroughs 140 and 141 extend from the interior of housing 14 to the exterior thereof, and permit electrical leads 18 to be connected electrically to the electronic circuitry disposed within housing 14.

The embodiment of sensor assembly 112 of the present invention illustrated in FIGS. 17(a), 17(b) and 18 includes intermediate metallization layer 39. The embodiment of the present invention illustrated in FIGS. 17(a), 17(b) and 18, therefore, provides higher amplitude output signals than is known in sensor assemblies of the present art owing to its unique bipolar electrode configuration.

Figure 19A:
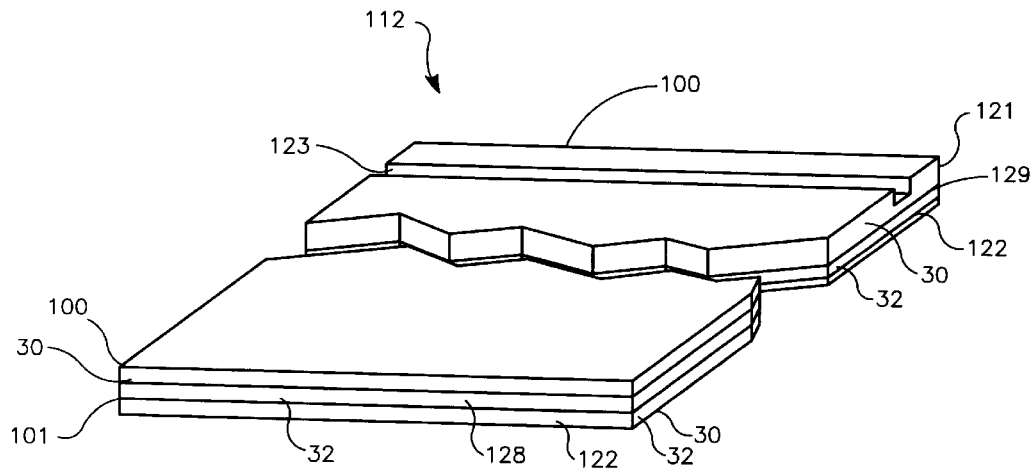
FIGS. 19(a) and 19(b) show selected views of another embodiment of a sensor of the present invention.
Figure 19B:
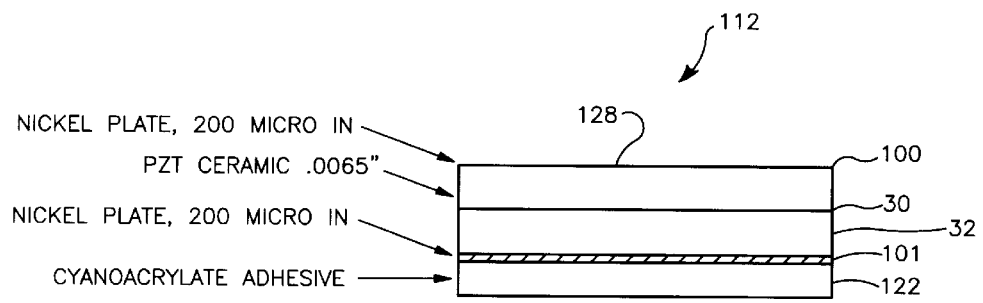

A more economical, albeit lower output embodiment of the present invention may be constructed by not including intermediate metallization layer 39 in sensor 112 shown in FIGS. 17(a), 17(b) and 18. In this alternative embodiment of the present invention, shown in FIGS. 19(a) and 19(b), rear or side nickel plating layer 121 remains disposed on rear edge 129 of sensor 112 and connects portions of top nickel layer 100 and bottom nickel layer 101. Notch 123 continues to electrically isolate portions of top nickel plating layer 100. Electrical connections A and B are established at the same locations shown in FIG. 18. This alternative embodiment of the present invention provides the significant advantages of reducing material and manufacturing costs and increasing fabrication yield owing to increased the simplicity of construction of a monopolar sensor.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Although specific embodiments of the invention have been set forth herein in some detail, it is to be understood that this has been done for the purposes of illustration only, and is not to be taken as a limitation on the scope of the invention as defined in the appended claims. It is to be understood that various alterations, substitutions, and modifications may be made to the embodiment described herein without departing from the spirit and scope of the appended claims. For example, a sensor or accelerometer having more than one intermediate metallization layer 39 falls within the scope of the present invention and the claims directed thereto. Such multiple intermediate metallization layers 39 could be employed to boost the output provided by a sensor or accelerometer. Interleaved and adjoining intermediate metallization layers could be electrically connected to poles having opposite polarity or the same polarity. A sensor or accelerometer having more than two sheets of piezoelectric material 30 and 32 also falls within the scope of the present invention and the claims directed thereto. Such additional sheet of piezoelectric material could be employed to separate a plurality of intermediate metallization layers 39, or to form each of sheets 30 and 32 from a plurality of individual sheets. Additionally, the scope of the present invention includes methods, and products made by such methods, of removing portions of an external electrically conductive layer to form at least first and second electrically conductive regions other than diamond wheel cutting, laser scribing, photo-etching or acid etching means. Such means include other chemical, laser, mechanical and abrasive removal means known to those skilled in the art.

We claim:

1. An implantable medical stimulator comprising a pulse generator, a sensor or accelerometer assembly mounted within the stimulator for providing a signal indicative of a patient's level of activity, and a control circuit responsive to the accelerometer signal for controlling operation of the pulse generator, the sensor assembly comprising:

a generally planar layer formed from a piezoelectric material, the layer having an upper surface, a lower surface and an outer edge, the outer edge extending between the upper surface and the lower surface, the upper surface and the outer edge forming an outer surface, and an external electrically conductive layer disposed on at least portions of the outer edge and extending between at least portions of the upper surface and portions of the lower surface, the external electrically conductive layer being electrically connected to the upper surface and the lower surface;

wherein at least portions of the external electrically conductive layer have been removed to form at least first and second electrically conductive regions that are electrically isolated from one another.

2. The implantable stimulator of claim 1, wherein the external electrically conductive layer comprises at least one metal selected from the group consisting of gold, silver, nickel, tungsten, molybdenum, palladium, platinum, osmium, iridium, technetium, rhenium, rhodium and ruthenium, and alloys, mixtures and combinations thereof.

3. The implantable stimulator of claim 1, wherein the generally planar layer comprises at least one of lead zirconate titanate, quartz, lithium niobate, and lithium titanate.

4. The implantable stimulator of claim 1, wherein the stimulator is one of a pacemaker, a defibrillator, a cardioverter and a pacer-cardioverter-defibrillator.

5. The implantable stimulator of claim 1, wherein the layer assumes a generally rectangular structural configuration.

6. The implantable stimulator of claim 1, wherein the accelerometer assembly further comprises an upper housing member and a lower housing member, the upper member having at least one downwardly facing bottom surface, the lower member having at least one upwardly facing top surface, the generally planar layer being disposed and housed between the upper and lower housing members.

7. The stimulator of claim 6, wherein at least one of the upper housing member and the lower housing member is formed of a material selected from the group consisting of Kovar, Alloy 42, copper, brass, aluminum, nickel, a noble metal, a carbon composite, a ceramic composition and a plastic.

8. The stimulator of claim 6, wherein at least one surface of the upper and lower housing members is plated with an electrically conductive metal or alloy.

9. The stimulator of claim 6, wherein at least one the upper and lower housing members is attached to a sheet of piezoelectric material by at least one of electrically conductive thermoplastic, epoxy and glue.

10. The implantable stimulator of claim 1, wherein the generally planar layer is disposed generally within an imaginary plane defined by two major substantially horizontal orthogonal axes and have formed therein a beam disposed along an imaginary longitudinal axis extending between first and second ends, the first and second layers having laterally extending outer members formed therein and adjacent at least the first end, the second end of the beam being deflectable along an imaginary vertical axis oriented substantially perpendicular to the plane.

11. The implantable stimulator of claim 10, wherein at least portions of the first upper surface and at least portions of the second lower surface are attached to at least one of the upper surface of the lower housing member and the lower surface of the upper housing member.

12. The implantable stimulator of claim 11, wherein at least one stop is disposed at a location above or below the second end of the beam, the stop limiting the vertical range of motion through which the beam deflects along the imaginary vertical axis to prevent failure, breakage or fracturing of the beam.

13. The stimulator of claim 12, wherein the stop forms a post or protrusion protruding from and disposed on one of the upper surface and the lower surface, respectively, of the upper housing member and the lower housing member.

14. The stimulator of claim 12, wherein the stop forms a post or protrusion protruding from and disposed on one of the upper surface and the lower surface, respectively, of the upper housing member and the lower housing member.

15. The stimulator of claim 12, wherein the stop forms a rail disposed on at least one of the upper surface and the lower surface, respectively, of the upper housing member and the lower housing member, the stop further being disposed in a direction perpendicular to the imaginary longitudinal axis.

16. The stimulator of claim 12, wherein the stop forms a T-shaped rail disposed on at least one of the upper surface and the lower surface, respectively, of the upper housing member and the lower housing member.

17. The stimulator of claim 12, wherein the stop forms a dab or blob of silicone disposed on at least one of the upper surface and the lower surface, respectively, of the upper housing member and the lower housing member.

18. The stimulator of claim 12, wherein the stop comprises a rail disposed on at least one of the upper surface and the lower surface, respectively, of the upper housing member and the lower housing member.

19. The stimulator of claim 18, wherein the stop is further disposed in a direction parallel to the imaginary longitudinal axis.

20. The stimulator of claim 18, wherein the rail is centrally disposed along the upper surface or the lower surface, respectively, of the upper or lower housing members.

21. The stimulator of claim 18, wherein the rail comprises a wide rail.

22. A method of making an accelerometer or sensor assembly for an implantable medical stimulator comprising a pulse generator, the accelerometer or sensor assembly being suitable for mounting within the stimulator and for providing a signal indicative of a patient's level of activity, the pulse generator comprising a control circuit responsive to the accelerometer signal for controlling operation of the pulse generator, for providing a signal indicative of a patients level of activity, the accelerometer assembly comprising a generally planar layer formed from a piezoelectric material, the first layer having a first upper surface, a first lower surface and a first outer edge, the first outer edge extending between the first upper surface and the first lower surface, the first upper surface and the first outer edge forming a first outer surface, the first generally planar layer forming a piezoelectric sub-assembly, and an external electrically conductive layer disposed on at least portions of the first outer surface, wherein portions of the external electrically conductive layer have been removed to form at least first and second electrically conductive regions that are electrically isolated from one another, the method comprising the steps of:

(a) providing the generally planar layer;
(b) disposing the external electrically conductive layer on at least portions of the first outer surface, and
(c) removing portions of the external electrically conductive layer to form the at least first and second electrically conductive regions, the first and second electrically conductive regions being electrically isolated from one another.

* * * * *